US012735430B2

(12) United States Patent
Vlahova et al.

(10) Patent No.: US 12,735,430 B2
(45) Date of Patent: Sep. 15, 2026

(54) CRYSTALLINE SOLVATED FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO [2,3-D]PYRIMIDIN-6-YL)PHENYL)-N'-METHOXYUREA

(71) Applicants: Sumitomo Pharma Co., Ltd., Osaka (JP); Richter Gedeon Nyrt., Budapest (HU)

(72) Inventors: Petinka I. Vlahova, West Lafayette, IN (US); Jennifer Nelson, Kokomo, IN (US); Michael Thomas Brandl, Redwood City, CA (US); Adrienn Szentes, Porva (HU); Zoltán Kazsu, Budapest (HU); Ádám Demeter, Budapest (HU)

(73) Assignees: Sumitomo Pharma Co., Ltd., Osaka (JP); Richter Gedeon Nyrt., Budapest (HU)

( * ) Notice: Subject to any disclaimer, the term of this patent is extended or adjusted under 35 U.S.C. 154(b) by 338 days.

(21) Appl. No.: 18/636,642

(22) Filed: Apr. 16, 2024

(65) Prior Publication Data

US 2025/0066382 A1 Feb. 27, 2025

Related U.S. Application Data

(63) Continuation of application No. PCT/EP2022/078989, filed on Oct. 18, 2022.

(60) Provisional application No. 63/257,073, filed on Oct. 18, 2021.

(51) Int. Cl.
*C07D 495/04* (2006.01)
*A61K 31/519* (2006.01)

(52) U.S. Cl.
CPC .......... *C07D 495/04* (2013.01); *A61K 31/519* (2013.01)

(58) Field of Classification Search
None
See application file for complete search history.

(56) References Cited

U.S. PATENT DOCUMENTS 3,872,115 A 3/1975 Sugimoto et al.
5,312,958 A 5/1994 Suenaga et al.
6,297,379 B1 10/2001 Furuya et al.
6,340,686 B1 1/2002 Furuya et al.
7,300,935 B2 11/2007 Cho et al.
7,569,570 B2 8/2009 Furuya et al.
8,058,280 B2 11/2011 Cho et al.
8,735,401 B2 5/2014 Cho et al.
9,346,822 B2 5/2016 Cho et al.
9,758,528 B2 9/2017 Fukuoka et al.
10,150,778 B2 12/2018 Miwa
10,160,765 B2 12/2018 Enlow et al.
10,350,170 B2 7/2019 Yamane et al.
10,449,191 B2 10/2019 Rajasekhar et al.
10,464,945 B2 11/2019 Miwa
10,544,160 B2 1/2020 Miwa
10,689,359 B2 6/2020 Shu et al.
10,786,501 B2 9/2020 Rajasekhar et al.
11,033,551 B2 6/2021 Johnson et al.
11,053,257 B2 7/2021 Miwa
11,583,526 B2 2/2023 Rajasekhar et al.
11,655,256 B1 5/2023 Paschalides
11,731,983 B2 8/2023 Miwa
11,793,812 B2 10/2023 Johnson et al.
11,795,178 B2 10/2023 Fukuoka et al.
11,957,684 B2 4/2024 Johnson et al.
12,097,198 B2 9/2024 Rajasekhar et al.
12,144,809 B1 11/2024 Rajasekhar et al.
12,180,224 B2 12/2024 Fukuoka et al.
12,325,714 B2 6/2025 Miwa
12,336,990 B2 6/2025 Rajasekhar et al.
12,338,249 B2 6/2025 Brandl et al.
2003/0055269 A1 3/2003 Fukuoka et al.
2004/0014634 A1 1/2004 Bantick et al.
2006/0160829 A1 7/2006 Cho et al.
2008/0287465 A1 11/2008 Tumey et al.
2009/0048273 A1 2/2009 Furuya et al.
2011/0172249 A1 7/2011 Kamikawa et al.
2015/0266891 A1 9/2015 Fukuoka et al.
2017/0210753 A1 7/2017 Fukuoka et al.
2019/0224196 A1 7/2019 Rajasekhar et al.
2019/0262346 A1 8/2019 Johnson et al.
2020/0000730 A1 1/2020 Yamane et al.
2022/0135585 A1 5/2022 Miwa
2022/0227784 A1 7/2022 Kantor et al.
2022/0372044 A1 11/2022 Jagusch et al.
2022/0396582 A1 12/2022 Brandl et al.
2023/0165800 A1 6/2023 Alonzo et al.
2023/0212184 A1 7/2023 Fukuoka et al.
(Continued)

FOREIGN PATENT DOCUMENTS

CA 3010509 A1 7/2017
CN 87101864 A 11/1987
(Continued)

OTHER PUBLICATIONS

Byrn, S. et al. (1995). “Pharmaceutical solids: A Strategic Approach to Regulatory Considerations,” Pharma. Res. 12:945-954.
(Continued)

*Primary Examiner* — Samantha L Shterengarts
(74) *Attorney, Agent, or Firm* — Cooley LLP

(57) ABSTRACT

This disclosure relates to crystalline solvated forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea. It also relates to methods of making the disclosed crystalline forms, pharmaceutical compositions and kits comprising the forms, and methods of treatment and uses comprising their administration.

24 Claims, 15 Drawing Sheets

(56) References Cited

U.S. PATENT DOCUMENTS

| | | | |
|---|---|---|---|
| 2024/0165118 | A1 | 5/2024 | Johnson et al. |
| 2025/0051353 | A1 | 2/2025 | Miwa |
| 2025/0057839 | A1 | 2/2025 | Rajasekhar et al. |
| 2025/0082632 | A1 | 3/2025 | Rajasekhar et al. |

FOREIGN PATENT DOCUMENTS

| | | | |
|---|---|---|---|
| CN | 1349536 | A | 5/2002 |
| CN | 1406239 | A | 3/2003 |
| CN | 1551883 | A | 12/2004 |
| CN | 1761671 | A | 4/2006 |
| CN | 1768065 | A | 5/2006 |
| CN | 101048065 | A | 10/2007 |
| CN | 110248661 | A | 9/2019 |
| CN | 111333633 | A | 6/2020 |
| CN | 111423452 | A | 7/2020 |
| CN | 112552312 | A | 3/2021 |
| CN | 115417883 | A | 12/2022 |
| CN | 115947734 | A | 4/2023 |
| EP | 1 266 898 | A1 | 12/2002 |
| EP | 1 591 446 | A1 | 11/2005 |
| EP | 3 666 776 | A1 | 6/2020 |
| IN | 31/2023 | | 8/2023 |
| JP | H-06-192170 | A | 7/1994 |
| JP | H-10-298156 | A | 11/1998 |
| JP | 2001-278884 | A | 10/2001 |
| JP | 2001-316391 | A | 11/2001 |
| JP | 2002-088044 | A | 3/2002 |
| JP | 2010-229098 | A | 10/2010 |
| JP | 2015-532262 | A | 11/2015 |
| JP | 2016-041720 | A | 3/2016 |
| JP | 2017-088564 | A | 5/2017 |
| JP | 2018-538348 | A | 12/2018 |
| JP | 2019-038825 | A | 3/2019 |
| JP | 2019-511510 | A | 4/2019 |
| WO | WO-00/56739 | A1 | 9/2000 |
| WO | WO-2004/067535 | A1 | 8/2004 |
| WO | WO-2007/011072 | A1 | 1/2007 |
| WO | WO-2010/026993 | A1 | 3/2010 |
| WO | WO-2014/051164 | A2 | 4/2014 |
| WO | WO-2014/051164 | A3 | 4/2014 |
| WO | WO-2016/136849 | A1 | 9/2016 |
| WO | WO-2017/172615 | A1 | 10/2017 |
| WO | WO-2018/060463 | A2 | 4/2018 |
| WO | WO-2018/060463 | A3 | 4/2018 |
| WO | WO-2018/060501 | A2 | 4/2018 |
| WO | WO-2018/060501 | A3 | 4/2018 |
| WO | WO-2019/178304 | A1 | 9/2019 |
| WO | WO-2020/0230094 | A1 | 11/2020 |
| WO | WO-2021/026011 | A1 | 2/2021 |
| WO | WO-2021/027937 | A1 | 2/2021 |
| WO | WO-2021/031148 | A1 | 2/2021 |
| WO | WO-2021/069700 | A1 | 4/2021 |
| WO | WO-2021/069711 | A1 | 4/2021 |
| WO | WO-2021/239917 | A1 | 12/2021 |
| WO | WO-2022/101303 | A1 | 5/2022 |
| WO | WO-2022/166121 | A1 | 11/2022 |
| WO | WO-2023/042214 | A1 | 3/2023 |
| WO | WO-2023/066941 | A1 | 4/2023 |
| WO | WO-2023/119333 | A1 | 6/2023 |
| WO | WO-2023/194924 | A1 | 10/2023 |

OTHER PUBLICATIONS

Caira, M.R. (1998). "Crystalline polymorphism of organic compounds," Topics in Curr. Chem. 198:163-208.
Chinese Office Action mailed on Nov. 17, 2016, for Chinese patent application No. 201380051107.2, filed on Sep. 27, 2013, 14 pages (with English translation).
Corrected Notice of Allowability mailed on Jul. 12, 2023, for U.S. Appl. No. 17/349,584, filed Jun. 16, 2021, 2 pages.
Corrected Notice of Allowability mailed on Sep. 1, 2023, for U.S. Appl. No. 17/694,635, filed Mar. 14, 2022, 2 pages.
Ding, Z. et al. (Oct. 22, 2018). "Crystalline forms," Chinese Pharmaceutical Journal, pp. 85 (with English Translation).
Ex Parte Quayle Action mailed on Jun. 5, 2018, for U.S. Appl. No. 15/481,505, filed Apr. 7, 2017, 4 pages.
Extended European Search Report mailed on Nov. 9, 2018, for EP Application No. 18 185 835.8, filed on Sep. 27, 2013, 5 pages.
Extended European Search Report mailed on Nov. 25, 2022, for EP Application No. 22 168 256.0, filed on Sep. 27, 2013, 8 pages.
Guo, Z. et al. (2003). "Synthesis and structure-activity relationships of Thieno[2,3-d]pyrimidine-2,4-dione derivatives as potent GnRH receptor antagonists," Bioorganic & Medicinal Chemistry Letters 13:3617-3622.
Holzer, G. et al. (1997). "K$\alpha_{1,2}$ and K$\beta_{1,3}$ x-ray emission lines of the 3d transition metals," Phys. Rev. A56(6):4554-4568.
International Search Report mailed on Mar. 24, 2014, for PCT Application No. PCT/JP2013/077013, filed on Sep. 27, 2013, 7 pages.
International Search Report mailed on Jan. 25, 2021, for PCT Application No. PCT/EP2020/078493, filed on Oct. 9, 2020, 6 pages.
International Search Report mailed on Jan. 25, 2021, for PCT Application No. PCT/EP2020/078475, filed on Oct. 9, 2020, 6 pages.
International Search Report mailed on Jan. 26, 2023, for PCT Application No. PCT/EP2022/078989, filed on Oct. 18, 2022, 4 pages.
Kumar, J.S. et al. (2001). "Simple and chemoselective reduction of aromatic nitro compounds to aromatic amines: Reduction with hydriodic acid revisited," Tetrahedron Letter 42:5601-5603.
Liu Xin-Yong et al. (2011). Laboratory Preparation, Separation and Purification Technology of Organic Compounds, People's Medical Publishing House, pp. 103-106 (with English translation).
Miwa, K. et al. (2011). "Discovery of 1-{4-[1-(2,6-Difluorobenzyl)-5-[(dimethylamino)methyl]-3-(6-methoxypyridazin-3-yl)-2,4-dioxo-1,2,3,4-tetrahydrothieno[2,3-d ]pyrimidin-6-yl]phenyl}-3-methoxyurea (TAK-385) as a Potent, Orally Active, Non-Peptide Antagonist of the Human Gonadotropin-Releasing Hormone Receptor," J. Med. Chem. 54:4998-5012.
Non-Final Office Action mailed on May 12, 2016, for U.S. Appl. No. 14/432,188, filed Mar. 27, 2015, 4 pages.
Non-Final Office Action mailed on Nov. 21, 2017, for U.S. Appl. No. 15/481,505, filed Apr. 7, 2017, 7 pages.
Non-Final Office Action mailed on Mar. 22, 2019, for U.S. Appl. No. 16/034,002, filed Jul. 12, 2018, 4 pages.
Non-Final Office Action mailed on Jun. 6, 2019, for U.S. Appl. No. 16/116,804, filed Aug. 29, 2018, 6 pages.
Non-Final Office Action mailed on Aug. 24, 2020, for U.S. Appl. No. 16/710,390, filed Dec. 11, 2019, 4 pages.
Non-Final Office Action mailed on Apr. 10, 2023, for U.S. Appl. No. 17/349,584, filed Jun. 16, 2021, 7 pages.
Non-Final Office Action mailed on Jul. 18, 2024, for U.S. Appl. No. 18/121,886, filed Mar. 15, 2023, 6 pages.
Notice of Allowance mailed on May 17, 2017, for U.S. Appl. No. 14/432,188, filed Mar. 27, 2015, 5 pages.
Notice of Allowance mailed on Sep. 17, 2018, for U.S. Appl. No. 15/481,505, filed Apr. 7, 2017, 5 pages.
Notice of Allowance mailed on Jul. 3, 2019, for U.S. Appl. No. 16/034,002, filed Jul. 12, 2018, 5 pages.
Notice of Allowance mailed on Sep. 12, 2019, for U.S. Appl. No. 16/116,804, filed Aug. 29, 2018, 6 pages.
Notice of Allowance mailed on Nov. 26, 2019, for U.S. Appl. No. 16/116,804, filed Aug. 29, 2018, 2 pages.
Notice of Allowance mailed on Mar. 10, 2021, for U.S. Appl. No. 16/710,390, filed Dec. 11, 2019, 6 pages.
Notice of Allowance mailed on May 10, 2023, for U.S. Appl. No. 17/349,584, filed Jun. 16, 2021, 5 pages.
Notice of Allowance mailed on Aug. 17, 2023, for U.S. Appl. No. 17/694,635, filed Mar. 14, 2022, 6 pages.
Notice of Allowance mailed on Aug. 21, 2024, for U.S. Appl. No. 18/121,886, filed Mar. 15, 2023, 5 pages.
Sasaki, S. et al. (2002). "Discovery of a thieno[2,3-d]pyrimidine-2,4-dione bearing a p-methoxyureidophenyl moiety at the 6-posi-

(56) References Cited

OTHER PUBLICATIONS tion: a highly potent and orally bioavailable non-peptide antagonist for the human luteinizing hormone-releasing hormone receptor ," J. Med. Chem. 46:113-124.
Written Opinion of the International Searching Authority mailed on Mar. 24, 2014, for PCT Application No. PCT/JP2013/077013, filed on Sep. 27, 2013, 10 pages.
Written Opinion of the International Searching Authority mailed on Jan. 25, 2021, for PCT Application No. PCT/EP2020/078493, filed on Oct. 9, 2020, 10 pages.
Written Opinion of the International Searching Authority mailed on Jan. 25, 2021, for PCT Application No. PCT/EP2020/078475, filed on Oct. 9, 2020, 11 pages.
Written Opinion of the International Searching Authority mailed on Jan. 26, 2023, for PCT Application No. PCT/EP2022/078989, filed on Oct. 18, 2022, 8 pages.
Yang, L.V. et al. (2009). Polymorphic Drugs, People's Medical Publishing House, pp. 24-25 (with English translation).
U.S. Appl. No. 17/349,584, filed Jun. 16, 2021, by Fukuoka et al.
U.S. Appl. No. 18/195,654, filed May 10, 2023, by Migoya et al.
U.S. Appl. No. 18/392,110, filed Dec. 21, 2023, by Migoya et al.
U.S. Appl. No. 18/427,033, filed Jan. 30, 2024, by Johnson et al.
U.S. Appl. No. 18/758,904, filed Jun. 28, 2024, by Rajasekhar et al.
U.S. Appl. No. 18/792,752, filed Aug. 2, 2024, by Rajasekhar et al.
U.S. Appl. No. 18/797,045, filed Aug. 7, 2024, by Migoya et al.
Non-Final Office Action mailed on Feb. 11, 2025, for U.S. Appl. No. 18/927,346, filed Oct. 25, 2024, 6 pages.
Notice of Allowance mailed on Feb. 20, 2025, for U.S. Appl. No. 17/716,963, filed Apr. 8, 2022, 9 pages.
U.S. Appl. No. 18/926,157, filed Oct. 24, 2024, by Johnson et al.
U.S. Appl. No. 19/086,039, filed Mar. 20, 2025, by Migoya et al.
Hirayama, N. (2008). Organic Compound Crystal Production Handbook, 32 pages (English Summary Provided).
Huang Li et al. (Nov. 18, 2018). "Progress in the study of new drug therapies for endometriosis," The Journal of Practical Medicine, vol. 34, No. 21, pp. 164-167 (with English Abstract Provided).
Serizawa, K. (2002). Optimization of salt and crystal forms and crystallization techniques, Pharm. Tech. Japan, vol. 18, No. 10, pp. 81-96 (with English Abstract Provided).
Zhang Hongli et al. (Dec. 31, 2016). "Microstructure and performance in the desolvation process of HNS/dioxane solvate by In-situ XRD method," Chinese Journal of Energetic Materials, vol. 24, No. 4, pp. 363-367 (with English Abstract Provided).
U.S. Appl. No. 18/927,346, filed Oct. 25, 2024, by Miwa.
U.S. Appl. No. 17/716,963, Corrected Notice of Allowability mailed on Apr. 16, 2025, Inventor Brandl, Michael Thomas et al., 6 pages.
U.S. Appl. No. 17/716,965, Non-Final Office Action mailed on May 12, 2025, Inventor Jagusch, Carsten et al., 10 pages.
U.S. Appl. No. 17/716,965, Non-Final Office Action mailed on Oct. 23, 2025, Inventor Jagusch, Carsten et al., 9 pages.
U.S. Appl. No. 19/201,728, filed May 7, 2025, Inventor Miwa, Kazuhiro.
U.S. Appl. No. 19/212,513, filed May 19, 2025, Inventor Brandl, Michael Thomas et al.
U.S. Appl. No. 19/228,661, filed Jun. 4, 2025, Inventor Johnson, Brendan Mark et al.

EtOH solvate
DMF solvate
THF solvate
Form II
Arbitrary y scale
θ-2θ (deg)
Image by PatternMatch v3.0.4

Intensity (cps)
0
50
100
150
200
2Theta (°)
5
10
15
20
25
30
35

CRYSTALLINE SOLVATED FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO [2,3-D]PYRIMIDIN-6-YL)PHENYL)-N'-METHOXYUREA

CROSS-REFERENCE TO RELATED APPLICATIONS

This application is a continuation of International Application No. PCT/EP2022/078989, filed Oct. 18, 2022, which claims the benefit of U.S. Provisional Application No. 63/257,073, filed Oct. 18, 2021, the disclosure of each of which is hereby incorporated by reference in its entirety.

BACKGROUND

Compound 1, N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, is a gonadotropin-releasing hormone (GnRH) antagonist approved for use as a pharmaceutical agent for treating various conditions including prostate cancer and heavy menstrual bleeding as well as other symptoms associated with uterine fibroids and is in development for the treatment of pain and other symptoms associated with endometriosis. Compound 1 may also be useful in the treatment of other diseases or disorders. See, e.g., U.S. Pat. Nos. 7,300,935, 8,058,280, 8,735,401, 9,346,822, 10,449,191, 10,786,501, and 11,033,551.

Compound 1 and methods of preparing Compound 1 are described in U.S. Pat. Nos. 7,300,935, 8,058,280, 8,735,401, 9,346,822, 9,758,528, 10,150,778, 10,464,945, 10,544,160, 11,053,257, U.S. patent application Ser. No. 17/349,584, U.S. Pat. No. 10,350,170, International Patent Application No. PCT/EP2021/064280, International Patent Publication No. WO2021/069711, and International Patent Publication No. WO2021/069700.

U.S. Pat. No. 9,758,528, which is herein incorporated by reference in its entirety, describes methods for producing Compound 1 and certain synthetic intermediates, as well as two crystalline forms of Compound 1: a crystal of a tetrahydrofuran (THF) solvate of Compound 1 and a crystal of an anhydrous form of Compound 1 (referred to herein as Form I of Compound 1). For reference, as detailed in U.S. Pat. No. 9,758,528, Form I of Compound 1 may be characterized by an X-ray powder diffraction (XRPD) pattern having peaks at approximately 7.4°, 8.9°, 9.9°, 12.1°, 16.6°, 17.3°, 22.2°, 22.8°, and 27.4° 2θ. Form I of Compound 1 begins to melt at about 189° C. and begins to degrade at about 197° C. Form I of Compound 1 shows an exothermic peak at about 237° C. by DSC with degradation at about 245° C. by TG International Patent Publication No. WO2021/069711, which is herein incorporated by reference in its entirety, describes methods for producing several crystalline forms of Compound 1, including: a second anhydrous form (referred to as Form II); a hemihydrate form (referred to as Form III); a toluene solvate (referred to as Form V); an anisole solvate (referred to as Form VI); an isopropanol solvate (referred to as Form VII); a dioxane solvate (referred to as Form VIII); a α, α, α-trifluorotoluene solvate (referred to as Form IX); a trifluoroethanol solvate (referred to as Form X); a DMF solvate (referred to as Form XI); and an acetone solvate (referred to as Form XII).

International Patent Publication No. WO2021/069700, which is herein incorporated by reference in its entirety, describes methods for producing a DMSO solvate crystalline form of Compound 1 (referred to as Form XIII).

SUMMARY

A crystalline form of an ethanol solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XIV of Compound 1 is disclosed herein. In some embodiments, Form XIV of Compound 1 is characterized by an X-ray powder diffraction pattern comprising at least three peaks selected from 7.31°, 8.38°, 9.96°, 10.69°, 15.43°, 19.02°, and 23.36° 2θ±0.2° 2θ. In some embodiments, Form XIV of Compound 1 is characterized by an X-ray powder diffraction pattern comprising at least five peaks selected from 7.31°, 8.38°, 9.96°, 10.69°, 15.43°, 19.02°, and 23.36° 2θ±0.2° 2θ. In some embodiments, Form XIV of Compound 1 is characterized by an X-ray powder diffraction pattern comprising at 7.31°, 8.38°, 9.96°, 10.69°, 15.43°, 19.02°, and 23.36° 2θ±0.2° 2θ.

Methods for preparing crystalline forms of an ethanol solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea are also disclosed herein. In some embodiments, methods for preparing such crystalline forms may include dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in dimethylformamide (DMF) to form a solution. The methods may also include adding the solution to ethanol to form a second solution. The methods may additionally include stirring the second solution to generate a suspension. The methods may also include isolating solids from the suspension to afford Form XIV of Compound 1.

Pharmaceutical compositions of a crystalline form of an ethanol solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea are also disclosed herein.

BRIEF DESCRIPTION OF THE DRAWINGS

FIG. 6A shows a full NMR spectrum indicating the presence of ethanol in the crystalline form. FIGS. 6B-6D are expanded regions of a full NMR spectrum.

DETAILED DESCRIPTION

Described herein are crystalline solvate forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (Compound 1), methods of making said forms, pharmaceutical compositions and kits comprising said forms, and methods of treatment and uses comprising their administration. The chemical structure of Compound 1 is as follows:

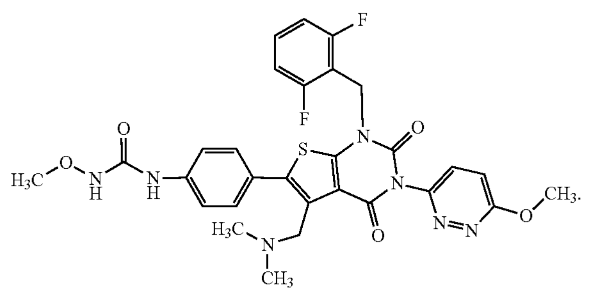 [SMILES: CONC(=O)Nc1ccc(-c2sc3c(c2CN(C)C)c(=O)n(-c2ccc(OC)nn2)c(=O)n3Cc2c(F)cccc2F)cc1]

General Information

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The Crystalline Form of the Disclosure

Form XIV is a crystalline ethanol solvate of Compound 1. As used herein, the term "solvate" includes stoichiometric solvates and non-stoichiometric solvates, such as channel-type solvates, formed by Compound 1 and a solvent. In some embodiments, suitable solvents may include, but are not limited to, ethanol.

Form XIV of Compound 1

Figure 1:
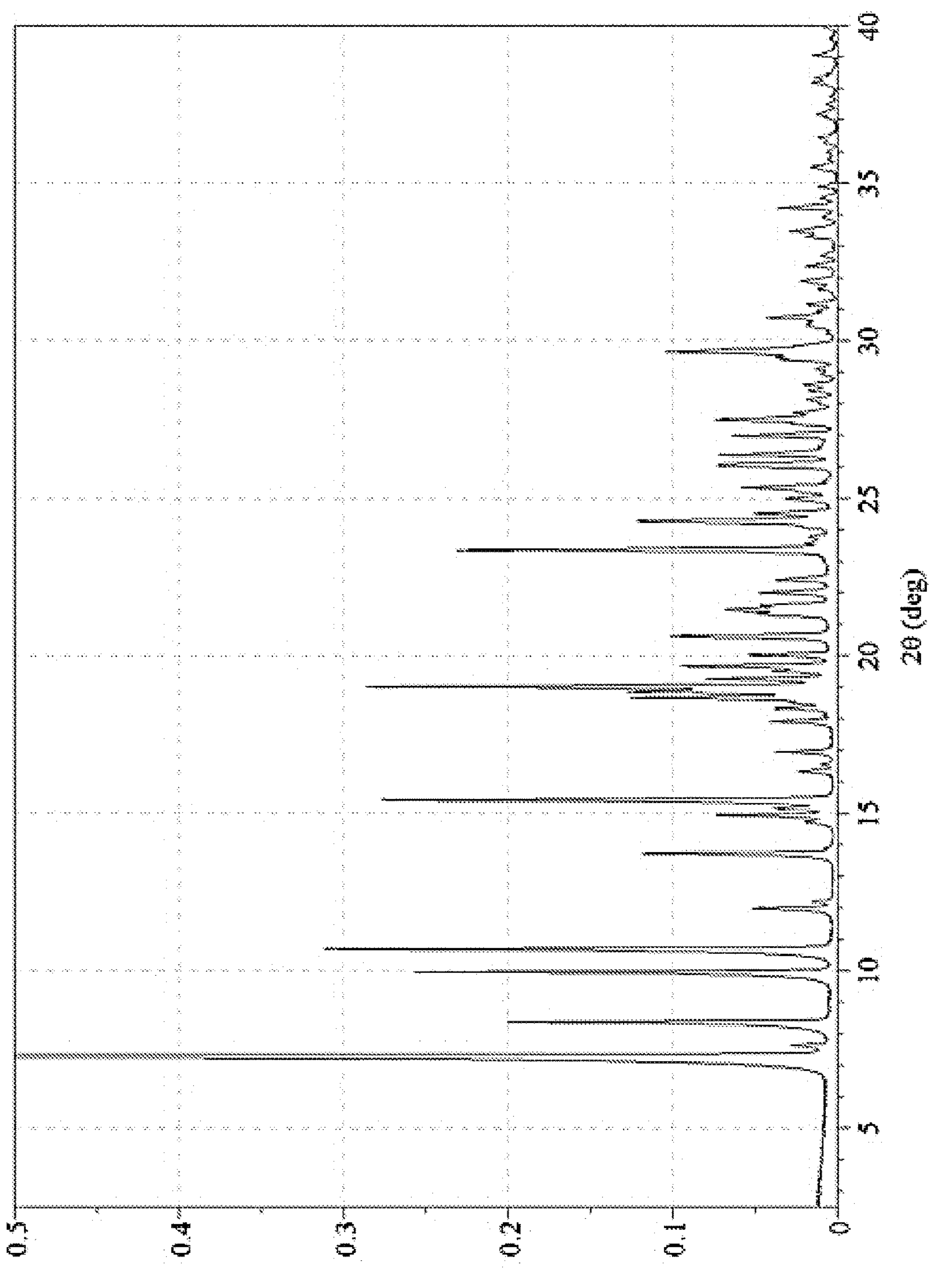
FIG. 1 depicts a powder X-ray diffraction pattern of Form XIV of Compound 1.

The present disclosure provides a crystalline form of Compound 1 characterized as Form XIV of Compound 1. In some embodiments, Form XIV of Compound 1 is an ethanol solvate. In some embodiments, Form XIV of Compound 1 is characterized by an X-ray powder diffraction (XRPD) pattern comprising at least one peak selected from the group consisting of 7.31°, 8.38°, 9.96°, 10.69°, 15.43°, 19.02°, and 23.36° 2θ±0.2° 2θ. In some embodiments, Form XIV of Compound 1 is characterized by an XRPD pattern comprising at least two peaks selected from the group consisting of 7.31°, 8.38°, 9.96°, 10.69°, 15.43°, 19.02°, and 23.36° 2θ±0.2° 2θ. In some embodiments, Form XIV of Compound 1 is characterized by an XRPD pattern comprising at least three peaks selected from the group consisting of 7.31°, 8.38°, 9.96°, 10.69°, 15.43°, 19.02°, and 23.36° 2θ±0.2° 2θ. In some embodiments, Form XIV of Compound 1 is characterized by an XRPD pattern comprising at least four peaks selected from the group consisting of 7.31°, 8.38°, 9.96°, 10.69°, 15.43°, 19.02°, and 23.36° 2θ±0.2° 2θ. In some embodiments, Form XIV of Compound 1 is characterized by an XRPD pattern comprising at least five peaks selected from the group consisting 7.31°, 8.38°, 9.96°, 10.69° 15.43°, 19.02°, and 23.36° 2θ±0.2° 2θ. In some embodiments, Form XIV of Compound 1 is characterized by an XRPD pattern comprising at least six peaks selected from the group consisting of 7.31°, 8.38°, 9.96°, 10.69°, 15.43°, 19.02°, and 23.36° 2θ±0.2° 2θ. In some embodiments, Form XIV of Compound 1 is characterized by an XRPD pattern comprising peaks at 7.31°, 8.38°, 9.96°, 10.69°, 15.43°, 19.02°, and 23.36° 2θ±0.2° 2θ. In some embodiments, Form XIV of Compound 1 is characterized by an XRPD pattern substantially the same as the pattern shown in FIG. 1.

In some embodiments, Form XIV of Compound 1 exhibits an XRPD pattern comprising peaks at 7.31°, 8.38°, 9.96°, 10.69°, 15.43°, 19.02°, and 23.36° 2θ±0.2° 2θ. In some embodiments, Form XIV of Compound 1 exhibits an XRPD pattern comprising peaks at 7.31°, 10.69°, and 15.43° 2θ±0.2° 2θ. In some embodiments, Form XIV of Compound 1 exhibits an XRPD pattern comprising peaks at 7.31°, 8.38°, 10.69°, and 15.43° 2θ±0.2° 2θ. In some embodiments, Form XIV of Compound 1 exhibits an XRPD pattern comprising peaks at 7.31°, 9.96°, 10.69°, and 15.43° 2θ±0.2° 2θ. In some embodiments, Form XIV of Compound 1 exhibits an XRPD pattern comprising peaks at 7.31°, 10.69°, 15.43°, and 19.02° 2θ±0.2° 2θ. In some embodiments, Form XIV of Compound 1 exhibits an XRPD pattern comprising peaks at 7.31°, 10.69°, 15.43°, and 23.36° 2θ±0.2° 2θ. In some embodiments, Form XIV of Compound 1 exhibits an XRPD pattern comprising peaks at 7.31°, 8.38°, 9.96°, 10.69°, and 15.43° 2θ±0.2° 2θ. In some embodiments, Form XIV of Compound 1 exhibits an XRPD pattern comprising peaks at 7.31°, 8.38°, 10.69°, 15.43° and 19.02° 2θ±0.2° 2θ. In some embodiments, Form XIV of Compound 1 exhibits an XRPD pattern comprising peaks at 7.31°, 8.38°, 10.69°, 15.43°, and 23.36° 2θ±0.2° 2θ. In some embodiments, Form XIV of Compound 1 exhibits an XRPD pattern comprising peaks at 7.31°, 9.96°, 10.69°, 15.43°, and 19.02° 2θ±0.2° 2θ. In some embodiments, Form XIV of Compound 1 exhibits an XRPD pattern comprising peaks at 7.31°, 9.96°, 10.69°, 15.43°, and 23.36° 2θ±0.2° 2θ. In some embodiments, Form XIV of Compound 1 exhibits an XRPD pattern comprising peaks at 7.31°, 10.69°, 15.43°, 19.02°, and 23.36° 2θ±0.2° 2θ.

In some embodiments, Form XIV of Compound 1 is characterized by an XRPD pattern comprising a peak having an approximate d-spacing value selected from the group consisting of 3.805 Å, 4.662 Å, 5.738 Å, 8.269 Å, and 12.083 Å. In some embodiments, Form XIV of Compound 1 is characterized by an XRPD pattern comprising at least two peaks having an approximate d-spacing value selected from the group consisting of 3.805 Å, 4.662 Å, 5.738 Å, 8.269 Å, 8.874 Å, 10.543 Å, and 12.083 Å. In some embodiments, Form XIV of Compound 1 is characterized by an XRPD pattern comprising at least three peaks having an approximate d-spacing value selected from the group consisting of 3.805 Å, 4.662 Å, 5.738 Å, 8.269 Å, 8.874 Å, 10.543 Å, and 12.083 Å. In some embodiments, Form XIV of Compound 1 is characterized by an XRPD pattern comprising at least four peaks having an approximate d-spacing value selected from the group consisting of 3.805 Å, 4.662 Å, 5.738 Å, 8.269 Å, 8.874 Å, 10.543 Å, and 12.083 Å. In some embodiments, Form XIV of Compound 1 is characterized by an XRPD pattern comprising at least five peaks having an approximate d-spacing value selected from the group consisting of 3.805 Å, 4.662 Å, 5.738 Å, 8.269 Å, 8.874 Å, 10.543 Å, and 12.083 Å. In some embodiments, Form XIV of Compound 1 is characterized by an XRPD pattern comprising at least six peaks having an approximate d-spacing value selected from the group consisting of 3.805 Å, 4.662 Å, 5.738 Å, 8.269 Å, 8.874 Å, 10.543 Å, and 12.083 Å. In some embodiments, Form XIV of Compound 1 is characterized by an XRPD pattern comprising peaks having approximate d-spacing values of 3.805 Å, 4.662 Å, 5.738 Å, 8.269 Å, 8.874 Å, 10.543 Å, and 12.083 Å.

In some embodiments, Form XIV of Compound 1 exhibits an XRPD pattern comprising peaks having approximate d-spacing values of 3.805 Å, 4.662 Å, 5.738 Å, 8.269 Å, 8.874 Å, 10.543 Å, and 12.083 Å. In some embodiments, Form XIV of Compound 1 exhibits an XRPD pattern comprising peaks having approximate d-spacing values of 5.738 Å, 8.269 Å, and 12.083 Å. In some embodiments, Form XIV of Compound 1 exhibits an XRPD pattern comprising peaks having approximate d-spacing values of 5.738 Å, 8.269 Å, 8.874 Å, and 12.083 Å. In some embodiments, Form XIV of Compound 1 exhibits an XRPD pattern comprising peaks having approximate d-spacing values of 5.738 Å, 8.269 Å, 10.543 Å, and 12.083 Å. In some embodiments, Form XIV of Compound 1 exhibits an XRPD pattern comprising peaks having approximate d-spacing values of 3.805 Å, 5.738 Å, 8.269 Å, and 12.083 Å. In some embodiments, Form XIV of Compound 1 exhibits an XRPD pattern comprising peaks having approximate d-spacing values of 4.662 Å, 5.738 Å, 8.269 Å, and 12.083 Å. In some embodiments, Form XIV of Compound 1 exhibits an XRPD pattern comprising peaks having approximate d-spacing values of 3.805 Å, 4.662 Å, 5.738 Å, 8.269 Å, and 12.083 Å. In some embodiments, Form XIV of Compound 1 exhibits an XRPD pattern comprising peaks having approximate d-spacing values of 3.805 Å, 5.738 Å, 8.269 Å, 8.874 Å, and 12.083 Å. In some embodiments, Form XIV of Compound 1 exhibits an XRPD pattern comprising peaks having approximate d-spacing values of 3.805 Å, 5.738 Å, 8.269 Å, 10.543 Å, and 12.083 Å. In some embodiments, Form XIV of Compound 1 exhibits an XRPD pattern comprising peaks having approximate d-spacing values of 4.662 Å, 5.738 Å, 8.269 Å, 8.874 Å, and 12.083 Å. In some embodiments, Form XIV of Compound 1 exhibits an XRPD pattern comprising peaks having approximate d-spacing values of 4.662 Å, 5.738 Å, 8.269 Å, 10.543 Å, and 12.083 Å. In some embodiments, Form XIV of Compound 1 exhibits an XRPD pattern comprising peaks at peaks having approximate d-spacing values of 5.738 Å, 8.269 Å, 8.874 Å, 10.543 Å, and 12.083 Å. In some embodiments, Form XIV of Compound 1 is isostructural with the tetrahydrofuran (THF) solvate of Compound 1 disclosed in U.S. Pat. No. 9,758,528.

Form XIV of Compound 1 may also be characterized by thermogravimetry (TG). In some embodiments, Form XIV of Compound 1 is characterized by a TG thermogram indicating a continuous weight loss of between about 2.0% and about 10.0% between about 49° C. and about 172° C. In some embodiments, Form XIV of Compound 1 is characterized by a TG thermogram indicating a continuous weight loss of between about 3.0% and about 9.0% between about 49° C. and about 172° C. In some embodiments, Form XIV of Compound 1 is characterized by a TG thermogram indicating a continuous weight loss of between about 4.0% and about 8.0% between about 49° C. and about 172° C. In some embodiments, Form XIV of Compound 1 is characterized by a TG thermogram indicating a continuous weight loss of between about 5.0% and about 7.0% between about 49° C. and about 172° C. In some embodiments, Form XIV of Compound 1 is characterized by a TG thermogram indicating a continuous weight loss of between about 5.5% and about 6.5% between about 49° C. and about 172° C. In some embodiments, Form XIV of Compound 1 is characterized by a TG thermogram indicating a continuous weight loss of about 6.0% between about 49° C. and about 172° C. In some embodiments, Form XIV of Compound 1 is characterized by a TG thermogram substantially the same as the pattern shown in FIG. 4.

Form XIV of Compound 1 may also be characterized by differential scanning calorimetry (DSC). In some embodiments, Form XIV of Compound 1 is characterized by an onset of melting between about 140° C. and about 145° C. In some embodiments, Form XIV of Compound 1 is characterized by an onset of melting of between about 141° C. and about 143° C. In some embodiments, Form XIV of Compound 1 is characterized by an onset of melting of between about 141.5° C. and about 142.5° C. In some embodiments, Form XIV of Compound 1 is characterized by an onset of melting at about 142° C. In some embodiments, Form XIV of Compound 1 is characterized by a differential scanning calorimetry (DSC) thermogram comprising an endothermic peak between about 145° C. and about 155° C. In some embodiments, Form XIV of Compound 1 is characterized by a differential scanning calorimetry (DSC) thermogram comprising an endothermic peak between about 147° C. and about 151° C. In some embodiments, Form XIV of Compound 1 is characterized by a differential scanning calorimetry (DSC) thermogram comprising an endothermic peak between about 148° C. and about 150° C. In some embodiments, Form XIV of Compound 1 is characterized by a differential scanning calorimetry (DSC) thermogram comprising an endothermic peak between about 148.5° C. and about 149.5° C. In some embodiments, Form XIV of Compound 1 is characterized by a DSC thermogram comprising an endothermic peak at about 149° C. In some embodiments, Form XIV of Compound 1 is characterized by a DSC thermogram substantially the same as the pattern shown in FIG. 5.

In some embodiments, Form XIV of Compound 1 is characterized by having at least two of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 148° C. and about 150° C. as measured by DSC.

In some embodiments, Form XIV of Compound 1 is characterized by having at least two of the following:

a) an XRPD pattern comprising at least three peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 148° C. and about 150° C. as measured by DSC.

In some embodiments, Form XIV of Compound 1 is characterized by having at least two of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting at about 142° C. as measured by DSC; and
d) an endothermic peak between about 148° C. and about 150° C. as measured by DSC.

In some embodiments, Form XIV of Compound 1 is characterized by having at least two of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 149° C. as measured by DSC.

In some embodiments, Form XIV of Compound 1 is characterized by having at least two of the following:

a) an XRPD pattern comprising at least three peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting at about 142° C. as measured by DSC; and
d) an endothermic peak at about 149° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 148° C. and about 150° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and
c) an endothermic peak between about 148° C. and about 150° C. as measured by DSC.

In some embodiments, Form XIV of Compound 1 is characterized by having each of the following:

a) an XRPD pattern comprising at least three peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 148° C. and about 150° C. as measured by DSC.

In some embodiments, Form XIV of Compound 1 is characterized by having each of the following:

a) an XRPD pattern comprising at least three peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and
c) an endothermic peak between about 148° C. and about 150° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting at about 142° C. as measured by DSC; and
d) an endothermic peak between about 148° C. and about 150° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and
c) an endothermic peak between about 148° C. and about 150° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;
c) an onset of melting between about 141° C. and about 143° C. as measured by DSC; and
d) an endothermic peak between about 149° C. as measured by DSC.

In some embodiments, Form XIV of Compound 1 is characterized by having each of the following:

a) an XRPD pattern comprising at least two peaks selected from the group consisting of 7.31°, 8.38°, 9.96°, 10.69°, 15.43°, 19.02°, and 23.36° 2θ±0.2° 2θ;
b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and c) an endothermic peak between about 149° C. as measured by DSC.

In some embodiments, Form XIV of Compound 1 is characterized by having each of the following:

a) an XRPD pattern comprising at least three peaks selected from the group consisting of 7.31°, 8.38°, 9.96°, 10.69°, 15.43°, 19.02°, and 23.36° 2θ±0.2° 2θ;

b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å;

c) an onset of melting at about 142° C. as measured by DSC; and d) an endothermic peak at about 149° C. as measured by DSC.

In some embodiments, Form XIV of Compound 1 is characterized by having each of the following:

a) an XRPD pattern comprising at least three peaks selected from the group consisting of 7.31°, 8.38°, 9.96°, 10.69°, 15.43°, 19.02°, and 23.36° 2θ±0.2° 2θ;

b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and c) an endothermic peak at about 149° C. as measured by DSC.

In some embodiments, a single crystal structure of Form XIV of Compound 1 has . . . .

In some embodiments, Form XIV of Compound 1 contains ethanol in an amount of about 1% to about 10% by weight relative to the total weight of Compound 1 present in Form XIV of Compound 1. In some embodiments, Form XIV of Compound 1 contains ethanol in an amount of about 5% to about 7% by weight relative to the total weight of Compound 1 present in Form XIV of Compound 1. In some embodiments, Form XIV of Compound 1 contains ethanol in an amount of about 5.5% to about 6.5% by weight relative to the total weight of Compound 1 present in Form XIV of Compound 1. In some embodiments, Form XIV of Compound 1 contains ethanol in an amount of about 6.0% by weight relative to the total weight of Compound 1 present in Form XIV of Compound 1.

Figure 6A:
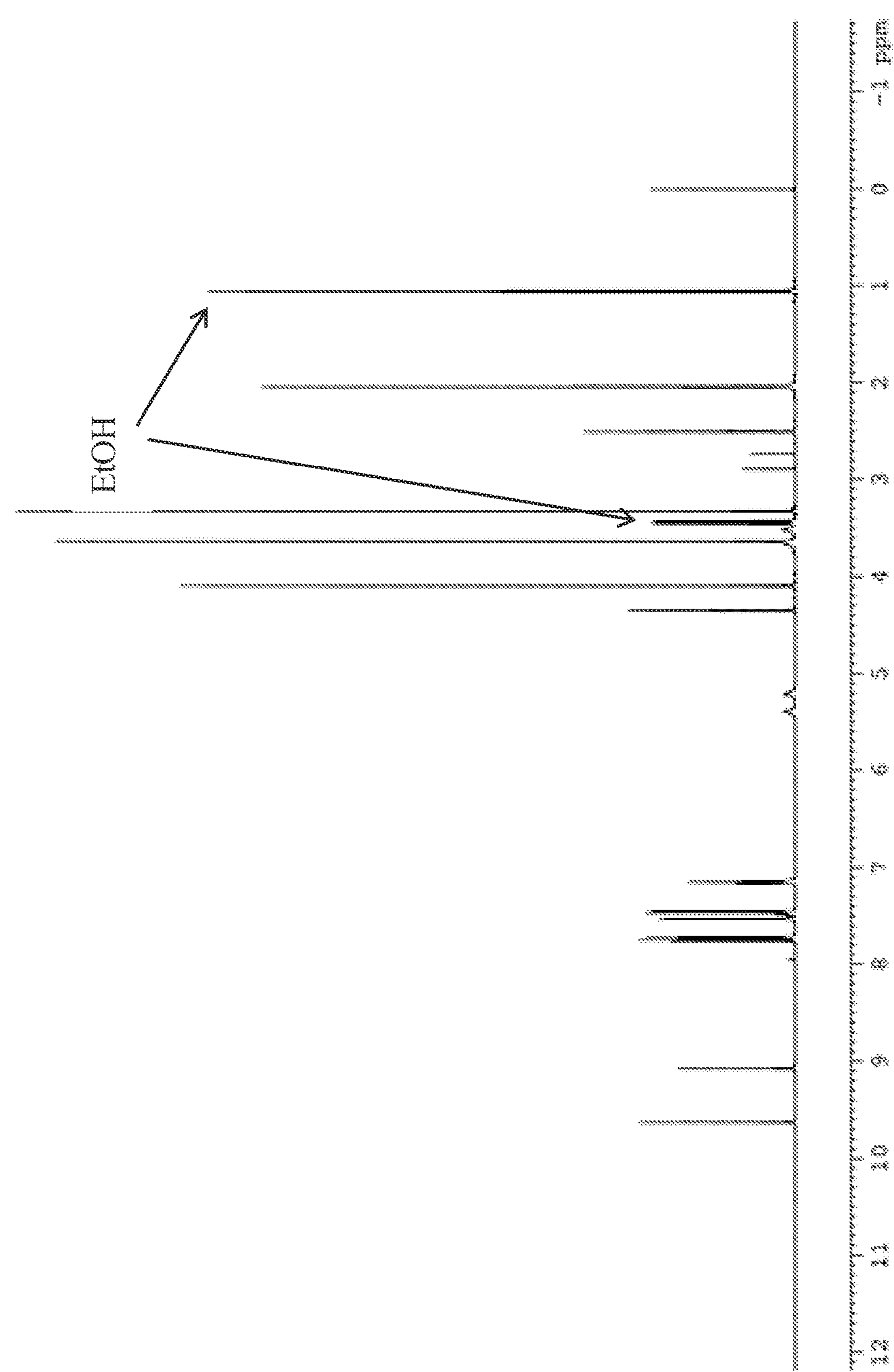
FIGS. 6A-D depict $^1$H NMR spectra (600 MHZ) of Form XIV of Compound 1 in dimethylsulfoxide-$d_6$.
Figure 6B:
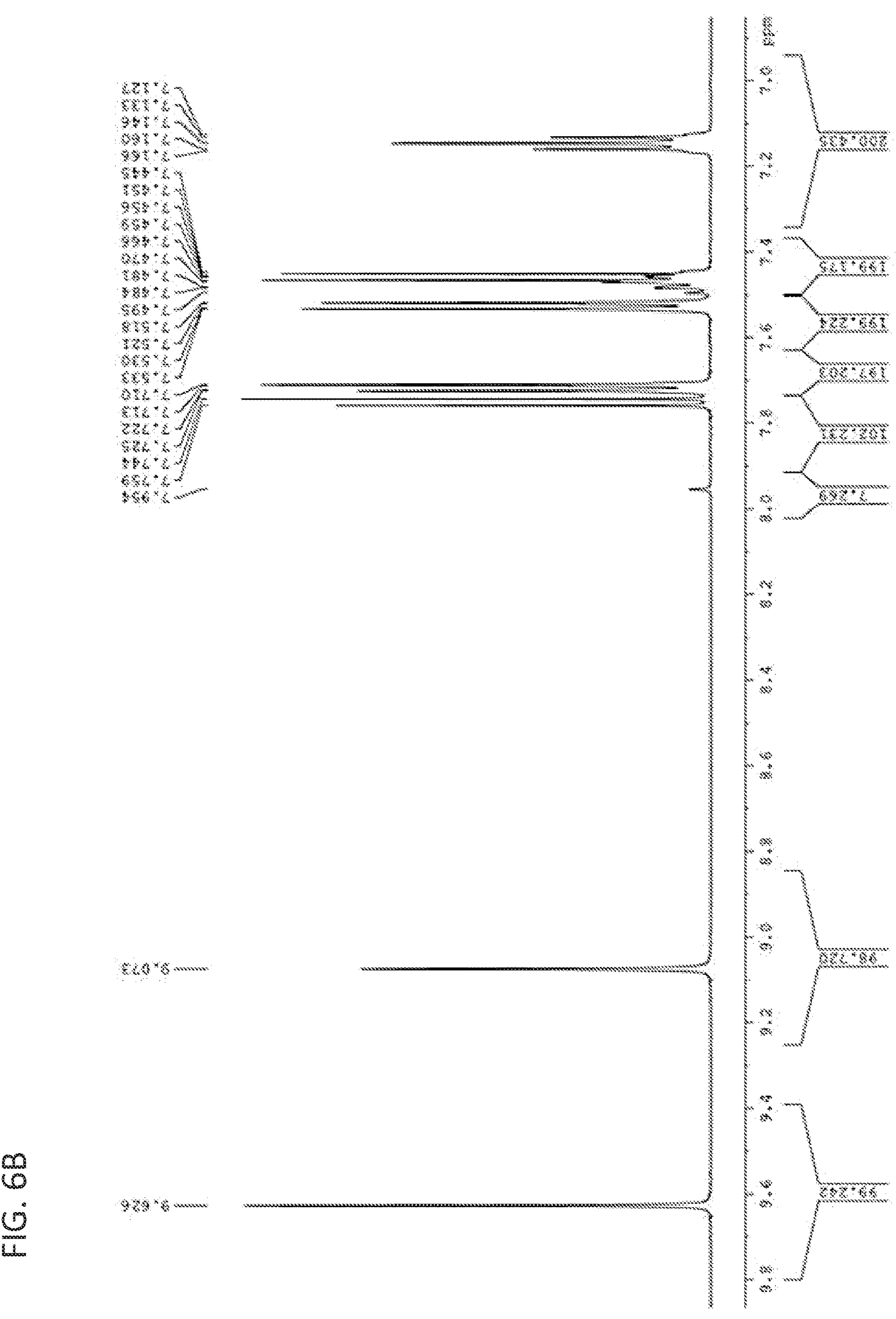
Figure 6C:
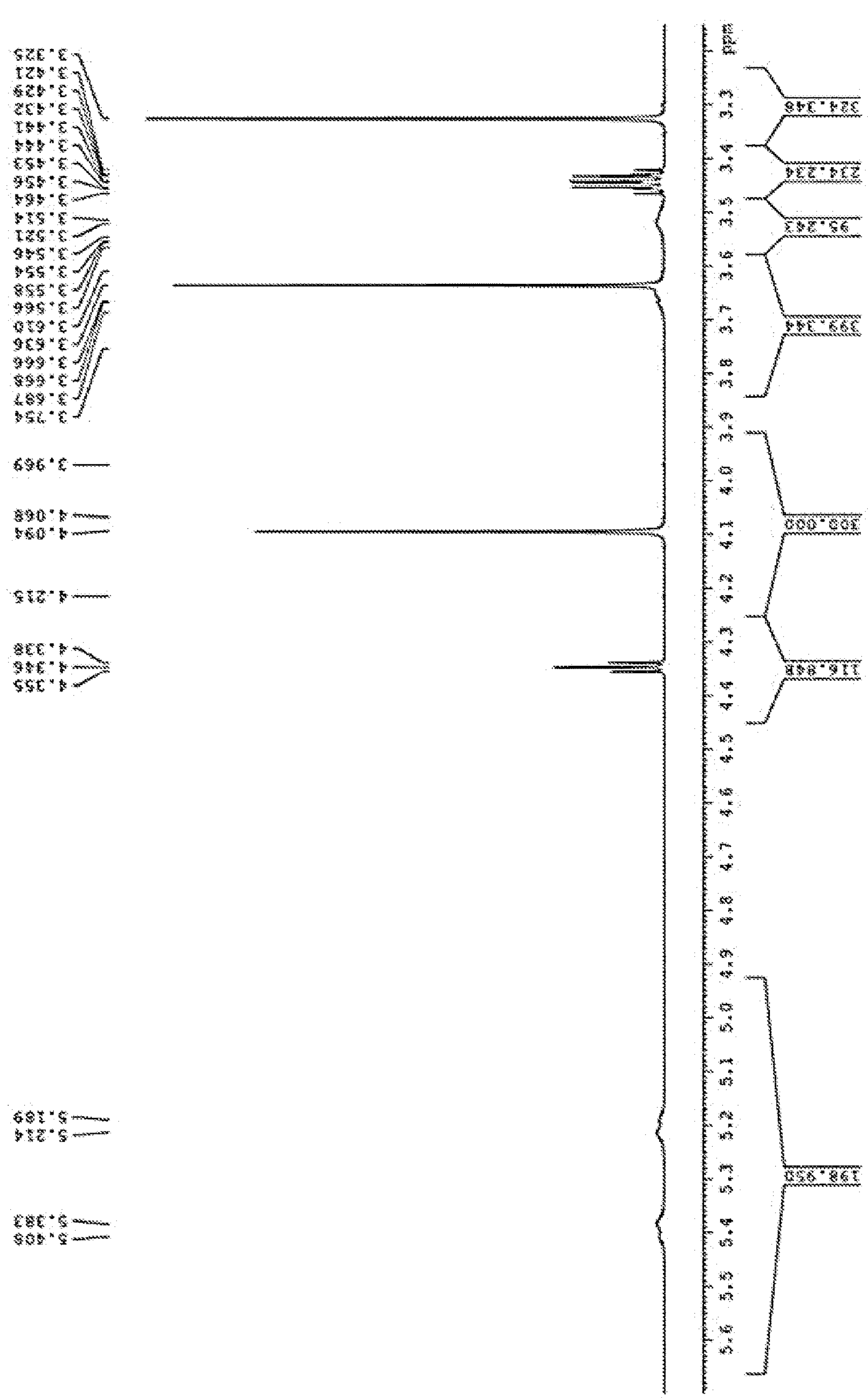
Figure 6D:
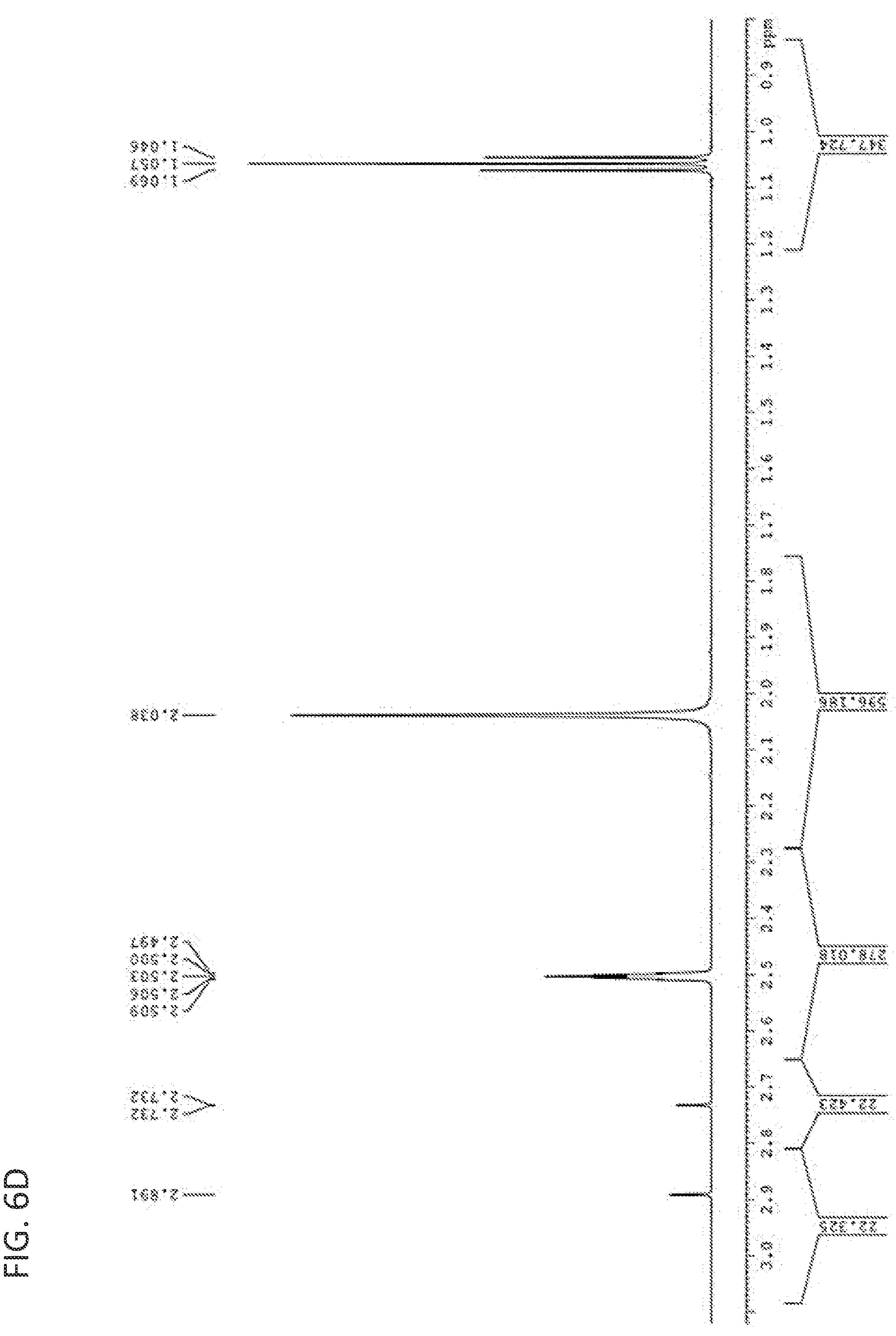

In some embodiments, Form XIV of Compound 1 contains ethanol in an amount of about 0.1 mol to about 1.5 mol, relative to 1 mol of Compound 1 present in Form XIV of Compound 1. In some embodiments, Form XIV of Compound 1 contains ethanol in an amount of about 0.5 mol to about 1.3 mol, relative to 1 mol of Compound 1 present in Form XIV of Compound 1. In some embodiments, Form XIV of Compound 1 contains ethanol in an amount of about 0.7 mol to about 1.1 mol, relative to 1 mol of Compound 1 present in Form XIV of Compound 1. In some embodiments, Form XIV of Compound 1 contains ethanol in an amount of about 0.8 mol to about 1.0 mol, relative to 1 mol of Compound 1 present in Form XIV of Compound 1. In some embodiments, Form XIV of Compound 1 contains ethanol in an amount of about 0.9 mol, relative to 1 mol of Compound 1 present in Form XIV of Compound 1. In some embodiments, Form XIV of Compound 1 is characterized by a $^1H$ NMR spectrum in DMSO-do that is substantially the same as the pattern shown in FIG. 6A.

In some embodiments, Form XIV of Compound 1 is substantially free of THF. As used herein "substantially free of THF" refers to an amount of THF that is not detectable using routine characterization techniques as would be familiar to the skilled artisan. In some embodiments, Form XIV of Compound 1 has less than about 720 ppm, less than about 500 ppm, less than about 300 ppm, less than about 250 ppm, or less than about 50 ppm THF.

In some embodiments, the Form XIV of Compound I disclosed herein may be characterized by XRPD patterns having the prominent peaks listed in Table 1. All peak listings are in degrees 2θ±0.2° 2θ.

TABLE 1

Prominent XRPD Peaks of Form XIV of Compound 1

| 2θ (°) ± 0.2° 2θ | d-spacing (Å) | Relative Intensity (%) |
|---|---|---|
| 7.31 | 12.083 ± 0.330 | 100 |
| 8.38 | 10.543 ± 0.251 | 21 |
| 9.96 | 8.874 ± 0.178 | 27 |
| 10.69 | 8.269 ± 0.154 | 32 |
| 15.43 | 5.738 ± 0.074 | 29 |
| 19.02 | 4.662 ± 0.049 | 30 |
| 23.36 | 3.805 ± 0.032 | 24 |

In some embodiments, the Form XIV of Compound I disclosed herein may be characterized by XRPD patterns having the observed peaks listed in Table 2. All peak listings are in degrees 2θ±0.2° 2θ. It should be understood that not all peaks may be observed due to their low relative intensity. In some embodiments of the Form XIV of Compound I disclosed herein, the Form XIV of Compound 1 has 1, 2, 3, 4, 5, 6, 7, 8, 9, 10, 11, 12, 13, 14, or 15 peaks listed in Table 2. In some embodiments, the Form XIV of Compound 1 has more than 15 of the peaks listed in Table 2.

TABLE 2

Observed XRPD Peaks of Form XIV of Compound 1

| 2θ (°) ± 0.2° 2θ | d-spacing (Å) | Relative Intensity (%) |
|---|---|---|
| 7.31 | 12.083 ± 0.330 | 100 |
| 7.65 | 11.547 ± 0.301 | 4 |
| 8.38 | 10.543 ± 0.251 | 21 |
| 9.96 | 8.874 ± 0.178 | 27 |
| 10.69 | 8.269 ± 0.154 | 32 |
| 11.98 | 7.382 ± 0.123 | 6 |
| 12.19 | 7.255 ± 0.119 | 2 |
| 13.71 | 6.454 ± 0.094 | 13 |
| 14.74 | 6.005 ± 0.081 | 3 |
| 14.95 | 5.921 ± 0.079 | 8 |
| 15.16 | 5.840 ± 0.077 | 5 |
| 15.43 | 5.738 ± 0.074 | 29 |
| 16.33 | 5.424 ± 0.066 | 3 |
| 16.56 | 5.349 ± 0.064 | 2 |
| 16.95 | 5.227 ± 0.061 | 5 |
| 17.91 | 4.949 ± 0.055 | 5 |
| 18.33 | 4.836 ± 0.052 | 5 |
| 18.50 | 4.792 ± 0.051 | 4 |
| 18.67 | 4.749 ± 0.050 | 13 |
| 18.86 | 4.701 ± 0.049 | 13 |
| 19.02 | 4.662 ± 0.049 | 30 |
| 19.26 | 4.605 ± 0.047 | 9 |
| 19.51 | 4.546 ± 0.046 | 5 |
| 19.67 | 4.510 ± 0.045 | 11 |
| 20.02 | 4.432 ± 0.044 | 6 |
| 20.62 | 4.304 ± 0.041 | 11 |
| 21.33 | 4.162 ± 0.039 | 6 |
| 21.46 | 4.137 ± 0.038 | 8 |
| 21.58 | 4.115 ± 0.038 | 6 |
| 22.00 | 4.037 ± 0.036 | 5 |
| 22.42 | 3.962 ± 0.035 | 4 |
| 23.36 | 3.805 ± 0.032 | 24 |
| 23.58 | 3.770 ± 0.032 | 3 |
| 23.77 | 3.740 ± 0.031 | 3 |
| 24.28 | 3.663 ± 0.030 | 13 |
| 24.52 | 3.628 ± 0.029 | 6 |

TABLE 2-continued

| Observed XRPD Peaks of Form XIV of Compound 1 | | |
|---|---|---|
| 2θ (°) ± 0.2° 2θ | d-spacing (Å) | Relative Intensity (%) |
| 24.98 | 3.562 ± 0.028 | 4 |
| 25.33 | 3.513 ± 0.027 | 7 |
| 26.05 | 3.418 ± 0.026 | 8 |
| 26.38 | 3.376 ± 0.025 | 8 |
| 26.99 | 3.301 ± 0.024 | 7 |
| 27.36 | 3.257 ± 0.023 | 4 |
| 27.49 | 3.242 ± 0.023 | 8 |
| 27.70 | 3.218 ± 0.023 | 4 |
| 28.00 | 3.184 ± 0.022 | 2 |
| 28.13 | 3.170 ± 0.022 | 3 |
| 28.41 | 3.139 ± 0.022 | 3 |
| 28.59 | 3.120 ± 0.021 | 3 |
| 28.93 | 3.083 ± 0.021 | 2 |
| 29.10 | 3.066 ± 0.021 | 2 |
| 29.39 | 3.037 ± 0.020 | 4 |
| 29.48 | 3.028 ± 0.020 | 5 |
| 29.64 | 3.012 ± 0.020 | 11 |

Preparation of Crystalline Forms of the Disclosure

Form XIV of Compound 1 may be used during the synthesis or production of Form I of Compound 1. Form I of Compound 1 and methods of preparing Form I of Compound 1 are described in U.S. Pat. No. 9,758,528, hereby incorporated by reference in its entirety, particular with regard to synthesis and crystallization methods. Methods of preparing Compound 1 before crystallization are described in U.S. Pat. Nos. 7,300,935, 8,058,280, 8,735,401, 9,346,822, 9,758,528, 10,150,778, 10,464,945, 10,544,160, 11,053,257, U.S. patent application Ser. No. 17/349,584, 10,350,170, International Patent Application No. PCT/EP2021/064280, International Patent Publication No. WO2021/069711, and International Patent Publication No. WO2021/069700, hereby incorporated by reference in their entireties.

In some embodiments, Form I of Compound 1 may be made by using Form XIV of Compound 1.

The disclosure provides a method for preparing Form XIV of Compound 1. In some embodiments, Form XIV of Compound 1 may be prepared from another form of Compound 1. In some embodiments, Form XIV of Compound 1 may be prepared from a crystalline form of Compound 1. In some embodiments, Form XIV of Compound 1 may be prepared from one or more of Form I of Compound 1, the THF solvate form of Compound 1, Form II of Compound 1, Form III of Compound 1, Form V of Compound 1, Form VI of Compound 1, Form VII of Compound 1, Form VIII of Compound 1, Form IX of Compound 1, Form X of Compound 1, Form XI of Compound 1, Form XII of Compound 1, and Form XIII of Compound 1. In some embodiments, Form XIV of Compound 1 may be prepared from one or more of Form I of Compound 1 and the THF solvate form of Compound 1.

In some embodiments, Form XIV of Compound 1 is prepared from Form I of Compound 1. In some embodiments, the method of preparing Form XIV of Compound 1 comprises dissolving Form I of Compound 1 in a polar solvent that is miscible with ethanol to give a solution. In some embodiments, the polar solvent is dimethylformamide (DMF). In some embodiments, the dissolution of Form I of Compound 1 in DMF is performed at room temperature.

In some embodiments, the method of preparing Form XIV of Compound 1 comprises adding the solution of Form I of Compound 1 to ethanol to form a second solution. In some embodiments, the second solution has an ethanol/polar solvent volume ratio of between about 85/15 and about 99/1 v/v. In some embodiments, the second solution has an ethanol/polar solvent volume ratio of between about 88/12 and about 98/2 v/v. In some embodiments, the second solution has an ethanol/polar solvent volume ratio of between about 90/10 and about 96/4 v/v. In some embodiments, the second solution has an ethanol/polar solvent volume ratio of between about 92/8 and about 94/6 v/v. In some embodiments, the second solution has an ethanol/polar solvent volume ratio of about 93/7 v/v.

In some embodiments, the method of preparing Form XIV of Compound 1 comprises stirring the second solution to generate a suspension. In some embodiments, the method of preparing Form XIV of Compound 1 isolating the solids from the suspension to afford Form XIV of Compound I. In some embodiments, the second solution is cooled before and/or during stirring.

In some embodiments, the second solution is kept at room temperature before stirring. In some embodiments, the second solution is cooled before stirring. In some embodiments, the second solution is cooled to between about 0° C. and −25° C. before stirring. In some embodiments, the second solution is cooled to between about 0° C. and −25° C.; 0° C. and −20° C.; 0° C. and −15° C.; 0° C. and −10° C.; 0° C. and −5° C.; −5° C. and −25° C.; −5° C. and −20° C.; −5° C. and −15° C.; −5° C. and −10° C.; −10° C. and −25° C.; −10° C. and −20° C.; −10° C. and −15° C.; −15° C. and −25° C.; −15° C. and −20° C.; or −20° C. and −25° C. before stirring. In some embodiments, the second solution is cooled to between about −10° C. and −25° C. for about 1 hour, about 2 hours, about 3 hours, about 6 hours, about 12 hours, about 18 hours, about 1 day, about 2 days, or about 3 days before stirring. In some embodiments, the second solution is cooled to between about −10° C. and −25° C. for about 1 day before stirring.

In some embodiments, the second solution is stirred for about 1 hour, about 2 hours, about 3 hours, about 6 hours, about 12 hours, about 18 hours, about 1 day, about 2 days, or about 3 days before stirring. In some embodiments, the second solution is stirred at room temperature. In some embodiments the second solution is cooled during stirring. In some embodiments, the second solution is cooled to between about −10° C. and −25° C. during stirring. In some embodiments, the second solution is cooled to between about 0° C. and −25° C.; 0° C. and −20° C.; 0° C. and −15° C.; 0° C. and −10° C.; 0° C. and −5° C.; −5° C. and −25° C.; −5° C. and −20° C.; −5° C. and −15° C.; −5° C. and −10° C.; −10° C. and −25° C.; −10° C. and −20° C.; −10° C. and −15° C.; −15° C. and −25° C.; −15° C. and −20° C.; or −20° C. and −25° C. during stirring. In some embodiments, the second solution is cooled to a temperature between about −10° C. and −25° C. for about 1 hour, about 2 hours, about 3 hours, about 6 hours, about 12 hours, about 18 hours, about 1 day, about 2 days, or about 3 days before stirring and is then stirred for about 1 hour, about 2 hours, about 3 hours, about 6 hours, about 12 hours, about 18 hours, about 1 day, about 2 days, or about 3 days at the temperature between about −10° C. and −25° C. In some embodiments, the second solution is cooled to a temperature between about −10° C. and −25° C. for about 1 day before stirring and is then stirred for about 1 day at the temperature between about −10° C. and −25° C.

In some embodiments the solids may be isolated by filtration. In some embodiments, the solids may be isolated by syringe filtration or vacuum filtration. In some embodiments, the solids may be isolated by syringe filtration. In some embodiments, the solids may be isolated by cold syringe filtration. In some embodiments, the filtration occurs at a temperature between about 0° C. and −25° C.

In some embodiments, the method of preparing Form XIV of Compound 1 comprises dissolving a crystalline form of N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea in ethanol (EtOH) to form a solution. In some embodiments, the crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is dissolved in EtOH at room temperature. In some embodiments, the crystalline form of N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea is dissolved in EtOH at reflux temperature. In some embodiments, the crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d] pyrimidin-6-yl)phenyl)-N'-methoxyurea is dissolved in EtOH at between about 0° C. and reflux temperature or between about 25° C. and reflux temperature. In some embodiments, the EtOH is free of other solvents.

In some embodiments, the solution of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in EtOH is cooled. In some embodiments, the solution is cooled to between about 5° C. and −10° C. In some embodiments, the solution is cooled to between about 5° C. and −5° C.; 5° C. and 0° C.; 0° C. and −10° C.; 0° C. and −5° C.; or −5° C. and −10° C. In some embodiments, the solution is cooled to about 5° C., 4° C., 3° C., 2° C., 1° C., 0° C., −1° C., −2° C., −3° C., −4° C., −5° C., −6° C., −7° C., −8° C., −9° C., and −10° C. In some embodiments, the solution is cooled over about 15 minutes, about 30 minutes, about 45 minutes, about 1 hour, or greater than about 1 hour.

In some embodiments the cooled solution of N-(4-(1-(2,6-difluorobenzyl)-5-((dimethylamino)methyl)-3-(6-methoxy-3-pyridazinyl)-2,4-dioxo-1,2,3,4-tetrahydrothieno [2,3-d]pyrimidin-6-yl)phenyl)-N'-methoxyurea in EtOH is stirred to generate a suspension. In some embodiments, the cooled solution is stirred for about 1, about 2, about 3, about 4, about 5, about 6, or more than about 6 hours.

In some embodiments, solids from the suspension are isolated to afford Form XIV of Compound 1. In some embodiments, the solids from the suspension are isolated by filtration (e.g., vacuum filtration). In some embodiments, the solids from the suspension are further dried. In some embodiments, the solids are dried at about 40° C. In some embodiments, the solids are dried at about 40° C. in a vacuum. In some embodiments, the solids are dried under a stream of inert gas (e.g., nitrogen). In some embodiments, the Form XIV of Compound 1 is free of other solvents.

Pharmaceutical Compositions

The disclosed crystalline Form XIV of Compound 1 may be used on its own but if administered to a subject will generally be administered in the form of a pharmaceutical composition in which Form XIV of Compound 1 is in association with a pharmaceutically acceptable carrier. Conventional procedures for the selection and preparation of suitable pharmaceutical compositions are described in, for example, "Pharmaceuticals—The Science of Dosage Form Designs," M. E. Aulton, Churchill Livingstone, 1988, which is hereby incorporated by reference in its entirety.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as a crystalline form of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., *Remington's Pharmaceutical Sciences*, Mack Publishing Co., Easton, Pa. 1975.

In some embodiments, the disclosure provides for a pharmaceutical composition comprising one or more crystalline forms disclosed herein. In some embodiments, the disclosure provides for a pharmaceutical composition comprising only one crystalline form disclosed herein. In some embodiments, the disclosure provides for a pharmaceutical composition comprising Form XIV of Compound 1. In other embodiments, the disclosure provides for a pharmaceutical composition comprising two crystalline forms disclosed herein. For example, a pharmaceutical composition comprising Compound 1 can comprise Form I of Compound 1 and Form XIV of Compound 1.

In some embodiments, the disclosure provides for a pharmaceutical composition comprising Form XIV of Compound 1 and a pharmaceutically acceptable carrier. In some embodiments, the disclosure provides for a pharmaceutical composition comprising Form I and Form XIV of Compound 1 and a pharmaceutically acceptable carrier.

Depending on the mode of administration, the pharmaceutical composition will comprise from about 0.05 to about 99 wt % (percent by weight), more particularly from about 0.05 to about 80 wt %, still more particularly from about 0.10 to about 70 wt %, and even more particularly from about 0.10 to about 50 wt % of one or more disclosed crystalline forms, all percentages by weight being based on total composition. In some embodiments, the pharmaceutical composition is administered transdermally, transmucosally, or topically (e.g., to the skin or to mucous membranes). In some embodiments, the pharmaceutical composition is administered as a vaginal suppository.

Pharmaceutical compositions of the present disclosure may comprise a therapeutically effective amount of one or more disclosed crystalline forms formulated together with one or more pharmaceutically acceptable carriers. Examples of pharmaceutically acceptable carriers include sugars such as lactose, dextrose, mannitol, glucose and sucrose; starches such as starches derived from corn, wheat or potato and other pharmaceutical grade starches such as sodium starch glycolate; cellulose and its derivatives such as sodium carboxymethyl cellulose, methyl cellulose, ethyl cellulose, hydroxypropyl cellulose, cellulose acetate, and microcrystalline cellulose; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; lubricants such as sodium lauryl sulfate and magnesium stearate; coloring agents; releasing agents; coating agents; sweetening, flavoring and perfuming agents; preservatives and antioxidants.

Provided herein are pharmaceutical compositions that are substantially free of THF.

Methods of Treatment and Uses

The present disclosure provides a method of treating a disorder comprising administering an effective amount of one or more crystalline forms, or one or more pharmaceutical compositions comprising said one or more crystalline forms, described herein to thereby treat the disorder in a subject in need thereof.

In some embodiments of the methods and uses of the disclosure, the disorder is a hormone-dependent condition. Hormone-dependent conditions may include sex hormone-dependent cancer (e.g., prostate cancer, uterine cancer, breast cancer, and ovarian cancer), bone metastasis of sex hormone-dependent cancer, prostatic hypertrophy, hysteromyoma (uterine fibroids), adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, heavy menstrual bleeding, and symptoms associated with these conditions. Such symptoms may include anemia, irregular periods, spotting, inflammation, pain, fatigue, urinary obstruction, urinary frequency, incontinence, constipation, anxiety, sleep disturbance, decrease in quality of life, difficulty with activities of daily living, female sexual dysfunction, and depression. In some embodiments of the methods and uses of the disclosure, the hormone-dependent condition is prostate cancer, uterine cancer, breast cancer, or ovarian cancer. Additional disorders that Compound 1 is useful for treating are described in U.S. Pat. Nos. 7,300,935, 8,058,280, 8,735,401, 9,346,822, 10,449,191, 10,786,501, and 11,033,551, which are incorporated herein by reference in their entireties.

In some embodiments of the methods and uses of the disclosure, the hormone-dependent condition is prostate cancer. In some embodiments of the methods and uses of the disclosure, the hormone-dependent condition is uterine cancer. In some embodiments of the methods and uses of the disclosure, the hormone-dependent condition is breast cancer. In some embodiments of the methods and uses of the disclosure, the hormone-dependent condition is ovarian cancer. In some embodiments of the methods and uses of the disclosure, the hormone-dependent condition is uterine fibroids. In some embodiments of the methods and uses of the disclosure, the hormone-dependent condition is heavy menstrual bleeding associated with uterine fibroids. In some embodiments of the methods and uses of the disclosure, the hormone-dependent condition is pain or other symptoms associated with uterine fibroids. In some embodiments of the methods and uses of the disclosure, the hormone-dependent condition is endometriosis. In some embodiments of the methods and uses of the disclosure, the hormone-dependent condition is pain associated with endometriosis. In some embodiments of the methods and uses of the disclosure, the hormone-dependent condition is adenomyosis. In some embodiments of the methods and uses of the disclosure, the hormone-dependent condition is heavy menstrual bleeding.

A “patient” or “subject” is a mammal. Examples of mammals may include, but are not limited to, any member of the class Mammalia including humans; non-human primates such as chimpanzees, monkeys, baboons, and rhesus monkeys; cattle, horses, sheep, goats, and swine; rabbits, dogs, and cats; and rodents such as rats, mice and guinea pigs. In some embodiments, the patient or subject is a human.

The terms “effective amount” or “therapeutically effective amount” when used in connection with one or more crystalline forms or pharmaceutical compositions of the disclosure may refer to a sufficient amount of the one or more crystalline forms or pharmaceutical compositions to provide the desired biological result. That result can be reduction and/or alleviation of the signs, symptoms, or causes of a disorder, or any other desired alteration of a biological system. For example, an “effective amount” for therapeutic use may be the amount of the one or more pharmaceutical compositions comprising the one or more crystalline forms as disclosed herein required to provide a clinically significant decrease in a disorder. An appropriate “effective amount” in any individual case may be determined by one of ordinary skill in the art using routine experimentation.

As used herein, the terms “treat” or “treatment” or cognates thereof, are meant to indicate a postponement of development of disorders; and/or reducing severity of such symptoms that will or are expected to develop. Thus, these terms may include ameliorating existing disorder symptoms; preventing additional symptoms; ameliorating or preventing the underlying causes of symptoms; inhibiting the disorder, e.g., arresting the development of the disorder; relieving the disorder; causing regression of the disorder; relieving a symptom caused by the disorder; or stopping or alleviating the symptoms of the disorder.

The terms “administered,” “administration,” or “administering” as used in this disclosure may refer to either directly administering one or more crystalline forms or pharmaceutical compositions of the disclosure to a subject.

The present disclosure provides a method of treating a disorder comprising administering an effective amount of Form XIV of Compound 1 to thereby treat the disorder in a subject in need thereof. The present disclosure provides a method of treating a disorder comprising administering an effective amount of a mixture of Forms I and XIV of Compound 1 to thereby treat the disorder in a subject in need thereof. In some embodiments, the disorder is a hormone-dependent condition.

The present disclosure provides a method of treating a disorder comprising administering an effective amount of one or more pharmaceutical compositions of the present disclosure to thereby treat the disorder in a subject in need thereof. In some embodiments, the present disclosure provides a method of treating a disorder comprising administering an effective amount of one or more pharmaceutical compositions comprising one or more crystalline forms disclosed herein to thereby treat the disorder in a subject in need thereof. In some embodiments, the present disclosure provides a method of treating a disorder comprising administering an effective amount of one or more pharmaceutical compositions comprising Form XIV of Compound 1 to thereby treat the disorder in a subject in need thereof. In some embodiments, the present disclosure provides a method of treating a disorder comprising administering an effective amount of one or more pharmaceutical compositions comprising a mixture of Forms I and XIV of Compound 1 to thereby treat the disorder in a subject in need thereof. In some embodiments, the disorder is a hormone-dependent condition.

The present disclosure provides one or more crystalline forms of the present disclosure or one or more pharmaceutical compositions of the present disclosure for use in treating a disorder in a subject in need thereof. In some embodiments, the one or more crystalline forms comprise Form XIV of Compound 1. In some embodiments, the one or more crystalline forms are a mixture of Forms I and XIV of Compound 1. In some embodiments, the one or more pharmaceutical compositions of the present disclosure comprise one or more crystalline forms disclosed herein. In some embodiments, the one or more pharmaceutical compositions of the present disclosure comprise Form XIV of Compound 1. In some embodiments, the one or more pharmaceutical compositions of the present disclosure comprise a mixture of Forms I and XIV of Compound 1. In some embodiments, the disorder is a hormone-dependent condition.

The present disclosure provides for use of one or more crystalline forms of the present disclosure for treating a disorder in a subject in need thereof. In some embodiments, the present disclosure provides for use of Form XIV of Compound 1 for treating a disorder in a subject in need thereof. In some embodiments, the present disclosure provides for use of a mixture of Forms I and XIV of Compound 1 for treating a disorder in a subject in need thereof. In some embodiments, the disorder is a hormone-dependent condition.

The present disclosure provides for use of one or more pharmaceutical compositions of the present disclosure for treating a disorder in a subject in need thereof. In some embodiments, the present disclosure provides for use of one or more pharmaceutical compositions comprising one or more crystalline forms disclosed herein for treating a disorder in a subject in need thereof. In some embodiments, the present disclosure provides for use of one or more pharmaceutical compositions comprising Form XIV of Compound 1 for treating a disorder in a subject in need thereof. In some embodiments, the present disclosure provides for use of one or more pharmaceutical compositions comprising a mixture of Forms I and XIV of Compound 1 for treating a disorder in a subject in need thereof. In some embodiments, the disorder is a hormone-dependent condition.

The present disclosure provides for use of one or more crystalline forms of the present disclosure in the manufacture of a medicament for treating a disorder. In some embodiments, the present disclosure provides for use of Form XIV of Compound 1 in the manufacture of a medicament for treating a disorder. In some embodiments, the present disclosure provides for use of a mixture of Forms I and XIV of Compound 1 in the manufacture of a medicament for treating a disorder. In some embodiments, the disorder is a hormone-dependent condition.

The present disclosure provides for use of one or more pharmaceutical compositions of the present disclosure in the manufacture of a medicament for treating a disorder. In some embodiments, the present disclosure provides for use of one or more pharmaceutical compositions comprising one or more crystalline forms disclosed herein in the manufacture of a medicament for treating a disorder. In some embodiments, the present disclosure provides for use of one or more pharmaceutical compositions comprising Form XIV of Compound 1 in the manufacture of a medicament for treating a disorder. In some embodiments, the present disclosure provides for use of one or more pharmaceutical compositions comprising a mixture of Forms I and XIV of Compound 1 in the manufacture of a medicament for treating a disorder. In some embodiments, the disorder is a hormone-dependent condition.

The present disclosure provides for use of one or more crystalline forms of the present disclosure as a medicament for treating a disorder. In some embodiments, the present disclosure provides for use of Form XIV of Compound 1 as a medicament for treating a disorder. In some embodiments, the present disclosure provides for use of a mixture of Forms I and XIV of Compound 1 as a medicament for treating a disorder. In some embodiments, the disorder is a hormone-dependent condition.

The present disclosure provides for use of one or more pharmaceutical compositions of the present disclosure as a medicament for treating a disorder. In some embodiments, the present disclosure provides for use of one or more pharmaceutical compositions comprising one or more crystalline forms disclosed herein as a medicament for treating a disorder. In some embodiments, the present disclosure provides for use of one or more pharmaceutical compositions comprising Form XIV of Compound 1 as a medicament for treating a disorder. In some embodiments, the present disclosure provides for use of one or more pharmaceutical compositions comprising a mixture of Forms I and XIV of Compound 1 as a medicament for treating a disorder. In some embodiments, the disorder is a hormone-dependent condition.

In some embodiments of the methods and uses of the disclosure, only one pharmaceutical composition of the disclosure is used in the methods or uses. In some embodiments of the methods and uses of the disclosure, only one crystalline form of the disclosure is used in the methods or uses.

For the therapeutic uses mentioned herein, the dosage administered will, of course, vary with the one or more crystalline forms or pharmaceutical compositions employed, the mode of administration, the treatment desired and the disorder indicated. For example, the daily dosage of the one or more crystalline forms of the present disclosure, if inhaled, may be in the range from about 0.05 micrograms per kilogram body weight (μg/kg) to about 100 micrograms per kilogram body weight (μg/kg). Alternatively, if the one or more crystalline forms or pharmaceutical compositions is administered orally, then the daily dosage of the one or more crystalline forms of the present disclosure may be in the range from about 0.01 micrograms per kilogram body weight (μg/kg) to about 100 milligrams per kilogram body weight (mg/kg).

It will be understood, however, that the total daily usage of the one or more crystalline forms or pharmaceutical compositions of the present disclosure will be decided by the attending physician within the scope of sound medical judgment. The specific therapeutically effective dose level for any particular patient will depend upon a variety of factors including the disorder being treated and the severity of the disorder; the activity of the specific crystalline form employed; the specific pharmaceutical composition employed; the age, body weight, general health, sex and diet of the patient; the time of administration, route of administration, and rate of excretion of the specific crystalline form employed; the duration of the treatment; drugs used in combination or coincidental with the specific crystalline form employed; and like factors well known in the medical arts. A physician or veterinarian of ordinary skill in the art can readily determine and prescribe the therapeutically effective amount of the one or more crystalline forms or pharmaceutical compositions disclosed herein required to treat, counter, or arrest the progress of the disorder.

Combination Therapy

In some embodiments, one or more crystalline forms or pharmaceutical compositions described herein may be used alone or together or conjointly administered, or used in combination, with one or more other therapeutic agents or pharmaceutical compositions. Conjoint administration or used in combination may refer to any form of administration of two or more different compounds, crystalline forms, or pharmaceutical compositions such that the second compound, crystalline form, or pharmaceutical composition is administered while the previously administered compound, crystalline form, or pharmaceutical composition is still effective in the body. For example, the different compounds, crystalline forms, or pharmaceutical compositions can be administered either in the same formulation or in a separate formulation, either simultaneously, sequentially, or by separate dosing of the individual components of the treatment. In some embodiments, the different compounds, crystalline forms, or pharmaceutical compositions can be administered within about one hour, about 12 hours, about 24 hours, about 36 hours, about 48 hours, about 72 hours, or about a week of one another. Thus, an individual who receives such treatment can benefit from a combined effect of different compounds, crystalline forms, or pharmaceutical compositions.

In some embodiments, one or more of the crystalline forms or pharmaceutical compositions of the disclosure are used in combination with one or more other crystalline forms or pharmaceutical compositions of the disclosure in the methods or uses of the disclosure. In certain such embodiments, the combination of one or more other crystalline forms or pharmaceutical compositions of the disclosure is used in a method for treating one or more of the disorders listed herein.

In some embodiments, one or more of the crystalline forms or pharmaceutical compositions of the disclosure are used in combination with estradiol or a corresponding amount of estradiol equivalent. In some embodiments, one or more of the crystalline forms or pharmaceutical compositions of the disclosure are used in combination with a progestin. In some embodiments, one or more of the crystalline forms or pharmaceutical compositions of the disclosure are used in combination with estradiol or a corresponding amount of estradiol equivalent and a progestin. In some embodiments, the progestin is norethindrone acetate.

In some embodiments, combinations of one or more crystalline forms or pharmaceutical compositions provided herein, or combinations of other known agents or pharmaceutical compositions and one or more crystalline forms or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more crystalline forms or pharmaceutical compositions of the disclosure are administered at a sub-therapeutic dose, wherein a subtherapeutic dose is a dose that would be insufficient to treat one of the disorders listed herein if administered alone.

Kits

In some embodiments, this disclosure also provides a pharmaceutical package or kit comprising one or more containers filled with at least one crystalline form or pharmaceutical composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The foregoing applies to any of the crystalline forms, pharmaceutical compositions, methods, and uses described herein. This disclosure specifically contemplates any combination of the features of such crystalline forms, pharmaceutical compositions, methods, and uses (alone or in combination) with the features described for the various kits described in this section.

Although methods and materials similar or equivalent to those described herein can be used in the practice or testing of the present disclosure, illustrative methods and materials are described herein. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

Emimerated Embodiments

Embodiment I-1. A crystalline form of an ethanol solvate of N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XIV of Compound 1.

Embodiment I-2. The crystalline form of embodiment I-1, characterized by an X-ray powder diffraction pattern comprising at least three peaks selected from 7.31°, 8.38°, 9.96°, 10.69°, 15.43°, 19.02°, and 23.36° 2θ±0.2° 2θ.

Embodiment I-3. The crystalline form of embodiments I-1 or I-2, characterized by an X-ray powder diffraction pattern comprising at least five peaks selected from 7.31°, 8.38°, 9.96°, 10.69°, 15.43°, 19.02°, and 23.36° 2θ±0.2° 2θ.

Embodiment I-4. The crystalline form of any one of embodiments I-1 to I-3, characterized by X-ray powder diffraction pattern comprising peaks at 7.31°, 8.38°, 9.96°, 10.69°, 15.43°, 19.02°, and 23.36° 2θ±0.2° 2θ.

Embodiment I-5. The crystalline form of any one of embodiments I-1 to I-4, characterized by an X-ray powder diffraction pattern substantially the same as the pattern shown in FIG. 1.

Embodiment I-6. The crystalline form of any one of embodiments I-1 to I-5, characterized by a thermogravimetric (TG) thermogram indicating continuous weight loss of about 6.0% between about 49° C. and about 172° C.

Embodiment I-7. The crystalline form of any one of embodiments I-1 to I-6, characterized by a TG thermogram substantially the same as the pattern shown in FIG. 4.

Embodiment I-8. The crystalline form of any one of embodiments I-1 to I-7, characterized by a differential scanning calorimetry (DSC) thermogram comprising an endothermic peak between about 147° C. and about 150° C.

Embodiment I-9. The crystalline form of any one of embodiments I-1 to I-8, characterized by a DSC thermogram comprising an endothermic peak at about 149° C.

Embodiment I-10. The crystalline form of any one of embodiments I-1 to I-19, characterized by a DSC thermogram substantially the same as the pattern shown in FIG. 5.

Embodiment I-11. The crystalline form of any one of embodiments I-1 to I-10, characterized by an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å.

Embodiment I-12. The crystalline form of embodiment I-1, characterized by having at least two of the following: (a) an X-ray powder diffraction pattern comprising at least three peaks selected from 7.31°, 8.38°, 9.96°, 10.69°, 15.43°, 19.02°, and 23.36° 2θ±0.2° 2θ; (b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and (c) an endothermic peak at about 149° C. as measured by DSC.

Embodiment I-13. The crystalline form of any one of embodiments I-1 to I-12, wherein said crystalline form is substantially free of tetrahydrofuran (THF).

Embodiment I-14. A pharmaceutical composition comprising the crystalline form of any one of embodiments I-1 to I-13.

Embodiment I-15. The pharmaceutical composition of embodiment I-14, wherein said composition is substantially free of (THF).

Embodiment I-16. A method for preparing the crystalline form of any one of embodiments I-1 to I-13 comprising: (a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in dimethylformamide (DMF) to form a solution; (b) adding the solution of step a) to ethanol to form a second solution; (c) stirring the second solution to generate a suspension; and (d) isolating solids from the suspension to afford Form XIV of Compound 1.

Embodiment I-17. The method of embodiment I-16, wherein the second solution is cooled to between about −10° C. and −25° C.

Embodiment I-18. The method of embodiment I-16 or I-17, wherein the second solution of step b) is cooled to between about −10° C. and −25° C., for 1 day.

Embodiment I-19. The method of any one of embodiments I-16 to I-18, wherein the stirring of step c) is carried between about −10° C. and −25° C.

Embodiment I-20. The method of any one of embodiments I-16 to I-19, wherein the isolating of step d) is accomplished using syringe filtration.

Embodiment I-21. A method for preparing the crystalline form of any one of embodiments I-1 I-14 comprising: (a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in ethanol (EtOH) to form a solution; (b) cooling the solution of step a); (c) stirring the cooled solution to generate a suspension; and (d) isolating solids from the suspension to afford Form XIV of Compound 1.

Embodiment I-22. The method of embodiment I-21, wherein the solution of step a) is cooled to between about 5° C. and −10° C.

Embodiment I-23. The method of embodiment I-21 or I-22, wherein the stirring of step c) is carried between about 5° C. and −10° C.

Embodiment I-24. The method of any one of embodiments I-21 to I-23, wherein the isolating of step d) is accomplished using filtration.

Embodiment II-22. A method of treating a disorder in a subject in need thereof, comprising administering to the subject an effective amount of the crystalline form of any one of embodiments I-1 to I-13.

Embodiment II-23. A method of treating a disorder in a subject in need thereof, comprising administering to the subject an effective amount of the pharmaceutical composition of embodiment I-14 or I-15.

Embodiment II-24. The method of embodiments II-22 to II-23, wherein the disorder is a hormone-dependent condition.

Embodiment II-25. The method of embodiment II-24, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment II-26. The method of embodiment II-24 or II-25, wherein the hormone-dependent condition is prostate cancer, uterine cancer, breast cancer, or ovarian cancer.

Embodiment II-27. The method of any one of embodiments II-24 to II-26, wherein the hormone-dependent condition is prostate cancer.

Embodiment II-28. The method of any one of embodiments II-24 to II-26, wherein the hormone-dependent condition is uterine cancer.

Embodiment II-29 The method of any one of embodiments II-24 to II-26, wherein the hormone-dependent condition is breast cancer.

Embodiment II-30. The method of any one of embodiments II-24 to II-26, wherein the hormone-dependent condition is ovarian cancer.

Embodiment II-31. The method of embodiment II-24, wherein the hormone-dependent condition is uterine fibroids.

Embodiment II-32. The method of embodiment II-24, wherein the hormone-dependent condition is heavy menstrual bleeding associated with uterine fibroids.

Embodiment II-33. The method of embodiment II-24, wherein the hormone-dependent condition is pain or other symptoms associated with uterine fibroids.

Embodiment II-35. The method of embodiment II-24 or II-25, wherein the hormone-dependent condition is endometriosis.

Embodiment II-36. The method of embodiment II-24 or II-25, wherein the hormone-dependent condition is adenomyosis.

Embodiment II-37. The method of embodiment II-24 or II-25, wherein the hormone-dependent condition is heavy menstrual bleeding.

Embodiment II-38. The method of any one of embodiments II-22 to II-37, the method comprising administering to the subject estradiol or a corresponding amount of estradiol equivalent.

Embodiment II-39. The method of any one of embodiments II-22 to II-38, the method comprising administering to the subject a progestin.

Embodiment II-40. The method of any one of embodiments II-22 to II-37, the method comprising administering to the subject estradiol, or a corresponding amount of estradiol equivalent, and a progestin.

Embodiment II-41. The method of embodiment II-39 or II-40, wherein the progestin is norethindrone acetate.

Embodiment II-42. A crystalline form of any one of embodiments I-1 to I-13, for use in treating a disorder in a subject in need thereof.

Embodiment II-43. The crystalline form for use of embodiment II-42, wherein the disorder is a hormone-dependent condition.

Embodiment II-44. The crystalline form for use of embodiment II-43, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment II-45. The crystalline form for use of any one of embodiments II-42 to II-44, wherein the hormone-dependent condition is prostate cancer, uterine cancer, breast cancer, or ovarian cancer.

Embodiment II-46. The crystalline form for use of any one of embodiments II-43 to II-45, wherein the hormone-dependent condition is prostate cancer.

Embodiment II-47. The crystalline form for use of any one of embodiments II-43 to II-45, wherein the hormone-dependent condition is uterine cancer.

Embodiment II-48. The crystalline form for use of any one of embodiments II-43 to II-45, wherein the hormone-dependent condition is breast cancer.

Embodiment II-49. The crystalline form for use of any one of embodiments II-43 to II-45, wherein the hormone-dependent condition is ovarian cancer.

Embodiment II-50. The crystalline form for use of embodiment II-43, wherein the hormone-dependent condition is uterine fibroids.

Embodiment II-51. The crystalline form for use of embodiment II-43, wherein the hormone-dependent condition is heavy menstrual bleeding associated with uterine fibroids.

Embodiment II-52. The crystalline form for use of embodiment II-43, wherein the hormone-dependent condition is pain or other symptoms associated with uterine fibroids.

Embodiment II-53. The crystalline form for use of embodiment II-43 or II-44, wherein the hormone-dependent condition is endometriosis.

Embodiment II-54. The crystalline form for use of embodiment II-43 or II-44, wherein the hormone-dependent condition is adenomyosis.

Embodiment II-55. The crystalline form for use of embodiment II-43 or II-44, wherein the hormone-dependent condition is heavy menstrual bleeding.

Embodiment II-56. The crystalline form for use of any one of embodiments II-42 to II-55, wherein the crystalline form for use is used in combination with estradiol or a corresponding amount of estradiol equivalent.

Embodiment II-57. The crystalline form for use of any one of embodiments II-42 to II-55, wherein the one or more crystalline forms for use are used in combination with progestin.

Embodiment II-58. The crystalline form for use of any one of embodiments II-42 to II-55, wherein the one or more crystalline forms for use are used in combination with estradiol, or a corresponding amount of estradiol equivalent, and a progestin.

Embodiment II-59. The crystalline form for use of embodiment II-57 or II-58, wherein the progestin is norethindrone acetate.

Embodiment II-60. A pharmaceutical composition of embodiment II-15 or II-16, for use in treating a disorder in a subject in need thereof.

Embodiment II-61. The pharmaceutical composition for use of embodiment II-60, wherein the disorder is a hormone-dependent condition.

Embodiment II-62. The pharmaceutical composition for use of embodiment II-61, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment II-63. The pharmaceutical composition for use of embodiment II-61 or II-62, wherein the hormone-dependent condition is prostate cancer, uterine cancer, breast cancer, or ovarian cancer.

Embodiment II-64. The pharmaceutical composition for use of any one of embodiments II-61 to II-63, wherein the hormone-dependent condition is prostate cancer.

Embodiment II-65. The pharmaceutical composition for use of any one of embodiments II-61 to II-63, wherein the hormone-dependent condition is uterine cancer.

Embodiment II-66. The pharmaceutical composition for use of any one of embodiments II-61 to II-63, wherein the hormone-dependent condition is breast cancer.

Embodiment II-67. The pharmaceutical composition for use of any one of embodiments II-61 to II-63, wherein the hormone-dependent condition is ovarian cancer.

Embodiment II-68. The pharmaceutical composition for use of embodiment II-61, wherein the hormone-dependent condition is uterine fibroids.

Embodiment II-69. The pharmaceutical composition for use of embodiment II-61, wherein the hormone-dependent condition is heavy menstrual bleeding associated with uterine fibroids.

Embodiment II-70. The pharmaceutical composition for use of embodiment II-61, wherein the hormone-dependent condition is pain or other symptoms associated with uterine fibroids.

Embodiment II-71. The pharmaceutical composition for use of embodiment II-61 or II-62, wherein the hormone-dependent condition is endometriosis.

Embodiment II-72. The pharmaceutical composition for use of embodiment II-61 or II-62, wherein the hormone-dependent condition is adenomyosis.

Embodiment II-73. The pharmaceutical composition for use of embodiment II-61 or II-62, wherein the hormone-dependent condition is heavy menstrual bleeding.

Embodiment II-74. The pharmaceutical composition for use of any one of embodiments II-60 to II-73, wherein the pharmaceutical composition for use is used in combination with estradiol or a corresponding amount of estradiol equivalent.

Embodiment II-75. The pharmaceutical composition for use of any one of embodiments II-60 to II-73, wherein the pharmaceutical composition for use is used in combination with a progestin.

Embodiment II-76. The pharmaceutical composition for use of any one of embodiments II-60 to II-73, wherein the pharmaceutical composition for use is used in combination with estradiol, or a corresponding amount of estradiol equivalent, and a progestin.

Embodiment II-77. The pharmaceutical composition for use of embodiment II-75 or II-76, wherein the progestin is norethindrone acetate.

Embodiment II-78. Use of the crystalline form of any one of embodiments I-1 to I-13 in the manufacture of a medicament for treating a disorder.

Embodiment II-79. Use of a pharmaceutical composition of embodiment I-14 or I-15 in the manufacture of a medicament for treating a disorder.

Embodiment II-80. Use of the crystalline form of any one of embodiments II-1 to II-13 as a medicament for treating a disorder.

Embodiment II-81. Use of a pharmaceutical composition of embodiment II-14 or I-15 as a medicament for treating a disorder.

Embodiment II-82. The use of any one of embodiments II-78 to II-81, wherein the disorder is a hormone-dependent condition.

Embodiment II-83. The use of embodiment II-82, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment II-84. The use of embodiment II-82 or II-83, wherein the hormone-dependent condition is prostate cancer, uterine cancer, breast cancer, or ovarian cancer.

Embodiment II-85. The use of any one of embodiments II-82 to II-84, wherein the hormone-dependent condition is prostate cancer.

Embodiment II-86. The use of any one of embodiments II-82 to II-84, wherein the hormone-dependent condition is uterine cancer.

Embodiment II-87. The use of any one of embodiments II-82 to II-84, wherein the hormone-dependent condition is breast cancer.

Embodiment II-88. The use of any one of embodiments II-82 to II-84, wherein the hormone-dependent condition is ovarian cancer.

Embodiment II-89. The use of embodiments II-82 to II-83, wherein the hormone-dependent condition is uterine fibroids.

Embodiment II-90. The use of embodiment II-82, wherein the hormone-dependent condition is heavy menstrual bleeding associated with uterine fibroids.

Embodiment II-91. The use of embodiment II-82, wherein the hormone-dependent condition is pain or other symptoms associated with uterine fibroids.

Embodiment II-92. The use of embodiment II-82 or II-83, wherein the hormone-dependent condition is endometriosis.

Embodiment II-93. The use of embodiment II-82 or II-83, wherein the hormone-dependent condition is adenomyosis.

Embodiment II-94. The use of embodiment II-82 or II-83, wherein the hormone-dependent condition is heavy menstrual bleeding.

Embodiment II-95. The use of any one of embodiments II-81 to II-94, the use comprising use of estradiol or a corresponding amount of estradiol equivalent for treating the disorder.

Embodiment II-96. The use of any one of embodiments II-81 to II-94, the use comprising use of a progestin for treating the disorder.

Embodiment II-97. The use of any one of embodiments II-81 to II-94, the use comprising use of estradiol, or a corresponding amount of estradiol equivalent, and a progestin for treating the disorder.

Embodiment II-98. The use embodiment II-96 or II-97, wherein the progestin is norethindrone acetate.

EXAMPLES

General Methods of the Examples

X-ray Powder Diffraction (XRPD)

X-ray powder diffractograms were with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640f) was analyzed to verify that the Si 111 peak position is consistent with the NIST-certified position. A specimen of the sample was sandwiched between 3 μm thick films and analyzed in transmission geometry. A beam-stop, short anti-scatter extension, and an anti-scatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5. Rounding algorithms were used to round each peak to the nearest 0.1° or 0.01° 2θ, depending upon the instrument used to collect the data and/or the inherent peak resolution. The location of the peaks along the x-axis (° 2θ) in both the figures and the tables were determined using proprietary software (TRIADS™ v2.1). Peak position variabilities are given to within ±0.2° 2θ based upon recommendations outlined in the USP discussion of variability in X-ray powder diffraction (United States Pharmacopeia, USP 42-NF 37 through S1, <941>, *Characterization of Crystalline and Partially Crystalline Solids by X-Ray Powder Diffraction* (*XRPD*), official from Aug. 1, 2019). For d-space listings, the wavelength used to calculate d-spacings was 1.5405929 Å, the Cu-Kα1 wavelength (*Phys. Rev*. A56 (6) 4554-4568 (1997)).

XRPD analysis of Example 2 was done using aPANalytical X'Pert PRO MPD diffractometer using an incident beam of Cu radiation produced using an Empyrean Cu LFF HR long, fine-focus source. A specimen of the sample was sandwiched between 6 μm thick Mylar® films and analyzed in transmission geometry. For d-space listings, the wavelength used to calculate d-spacings was 1.5405980 Å for the Cu-Kα1 wavelength.

Differential Scanning Calorimeter (DSC)

The DSC analyses were performed using a Mettler-Toledo TGA/DSC3+ analyzer. The temperature and enthalpy were adjusted with indium, tin and zinc. The adjustment was then verified with indium and the balance was verified with calcium oxalate. The sample was placed in an tared, open aluminum pan. The weight of the sample was determined, then the pan was hermetically sealed, the lid pierced, and then inserted into the furnace. The furnace was heated under nitrogen and data was collected from 25° C. to 350° C. at 10° C./min.

DSC analysis of Example 2 was done using a TA Instruments Discovery DSC 2500 instrument. The temperature and enthalpy calibration were done with indium and tin standards. The sample was placed in an open aluminum pan and the weight accurately recorded. The pan was then inserted into the DSC instrument's autosampler tray from where it was placed to the sample platform. A weighed, empty aluminum sample pan was placed on the reference platform. The DSC cell was heated under 50 ml/min nitrogen flow and data was collected from 30° C. to 260° C. at 10° C./min Thermogravimetry (TG)

The TG analyses were performed using a Mettler-Toledo TGA/DSC3+ analyzer. The temperature and enthalpy were adjusted with indium, tin and zinc. The adjustment was then verified with indium and the balance was verified with calcium oxalate. The sample was placed in an tared, open aluminum pan. The weight of the sample was determined, then the pan was hermetically sealed, the lid pierced, and then inserted into the furnace. The furnace was heated under nitrogen and data was collected from 25° C. to 350° C. at 10° C./min.

TG analysis of Example 2 was done using a TA Instruments Discovery TGA 5500 instrument. The temperature calibration was done using alumel and nickel Curie temperature standards. The sample was placed in an open platinum sample pan. The pan was then inserted into the TG instrument's autosampler tray from where it was placed on the balance's sample hangdown wire. An empty platinum sample pan was placed on the balance's reference platinum hangdown wire. The furnace was heated under 25 ml/min nitrogen flow and data was collected from ambient temperature to 260° C. at 10° C./min.

Proton Nuclear Magnetic Resonance ($^1$H NMR)

$^1$H NMR spectra were obtained with an Avance 600 MHz NMR spectrometer. Samples were prepared by dissolving approximately 5-10 mg of the material to be characterized in dimethyl sulfoxide-$d_6$ (DMSO-$d_6$). Spectra were calibrated to an internal tetramethylsilane (TMS) reference.

Preparation and Characterization of Form XIV of Compound 1

Form XIV of Compound 1

The disclosure provides methods for preparing Form XIV of Compound 1.

Example 1: Form I of Compound 1 (118.6 mg) was dissolved in DMF (0.4 mL) at ambient temperature. The solution was filtered through a 0.2 μm nylon filter into a vial containing EtOH (5 mL). The resulting solution was left unstirred and placed in a freezer for one day. The clear solution that resulted was then stirred for one day between −10° C. to −25° C. to provide a slurry. The solids were isolated cold by syringe filtration using a cold syringe and filter to yield Form XIV of Compound 1. These conditions are summarized in Table 3, below.

Comparative Examples 1-4: The conditions of several comparative examples, which failed to yield Form XIV of Compound 1, are summarized in Table 3, below.

TABLE 3

| Example Conditions | | | |
|---|---|---|---|
| Example No. | Starting Form of Compound 1 | Conditions | Resulting Form of Compound 1 |
| Example 1 | Form I | 1. Form I was dissolved in DMF to give a solution.<br>2. The solution was added to EtOH (EtOH/DMF ratio = 93/7 v/v) to give a clear solution.<br>3. The clear solution was placed in a freezer. It was left unstirred for 1 day.<br>4. The solution was then stirred in the freezer for 1 day to produce a precipitate.<br>5. Filtered cold to isolate solid Form XIV. | Form XIV |
| Comparative Example 1 | Form I | 1. Form I was suspended in EtOH at 65° C. and stirred. Form I remained undissolved.<br>2. The suspension was filtered to yield a clear solution.<br>3. Solution was slow-cooled to room temperature, 3° C./h. Attempted to seed with THF solvate at 65° C. but seeds appeared to dissolve.<br>4. The solution was cooled to room temperature.<br>5. Solution was then seeded with the THF solvate of Compound 1. Seeds held.<br>6. Stirred at room temperature for 4 days. | Form I |
| Comparative Example 2 | Form I | 1. Form I was dissolved in DMF.<br>2. The solution was added to EtOH. EtOH/DMF ratio: 88/12 v/v. A clear solution resulted<br>3. The solution as stirred at room temperature for 2 hours. | Form I |
| Comparative Example 3 | THF Solvate | 1. The THF solvate of Compound 1 was added to EtOH at 40° C. for 1 hour.<br>2. The solids appeared to partially dissolve and then precipitate.<br>3. The slurry was stirred at room temperature for 3 hours. | Form I |

TABLE 3-continued

| Example Conditions | | | |
|---|---|---|---|
| Example No. | Starting Form of Compound 1 | Conditions | Resulting Form of Compound 1 |
| | | 4. The solvent was decanted of the solid, and fresh ethanol was added.<br>5. The resulting slurry was stirred at room temperature for 4 days.<br>6. The solid was collected by filtration and washed with ethanol. | |
| Comparative Example 4 | THF Solvate | 1. The THF solvate of Compound 1 was added to EtOH.<br>2. The resulting slurry was stirred at room temperature for 3 days.<br>3. The solid was analyzed wet. | Form I |

XRPD Characterization of Form XIV of Compound 1

Figure 2:
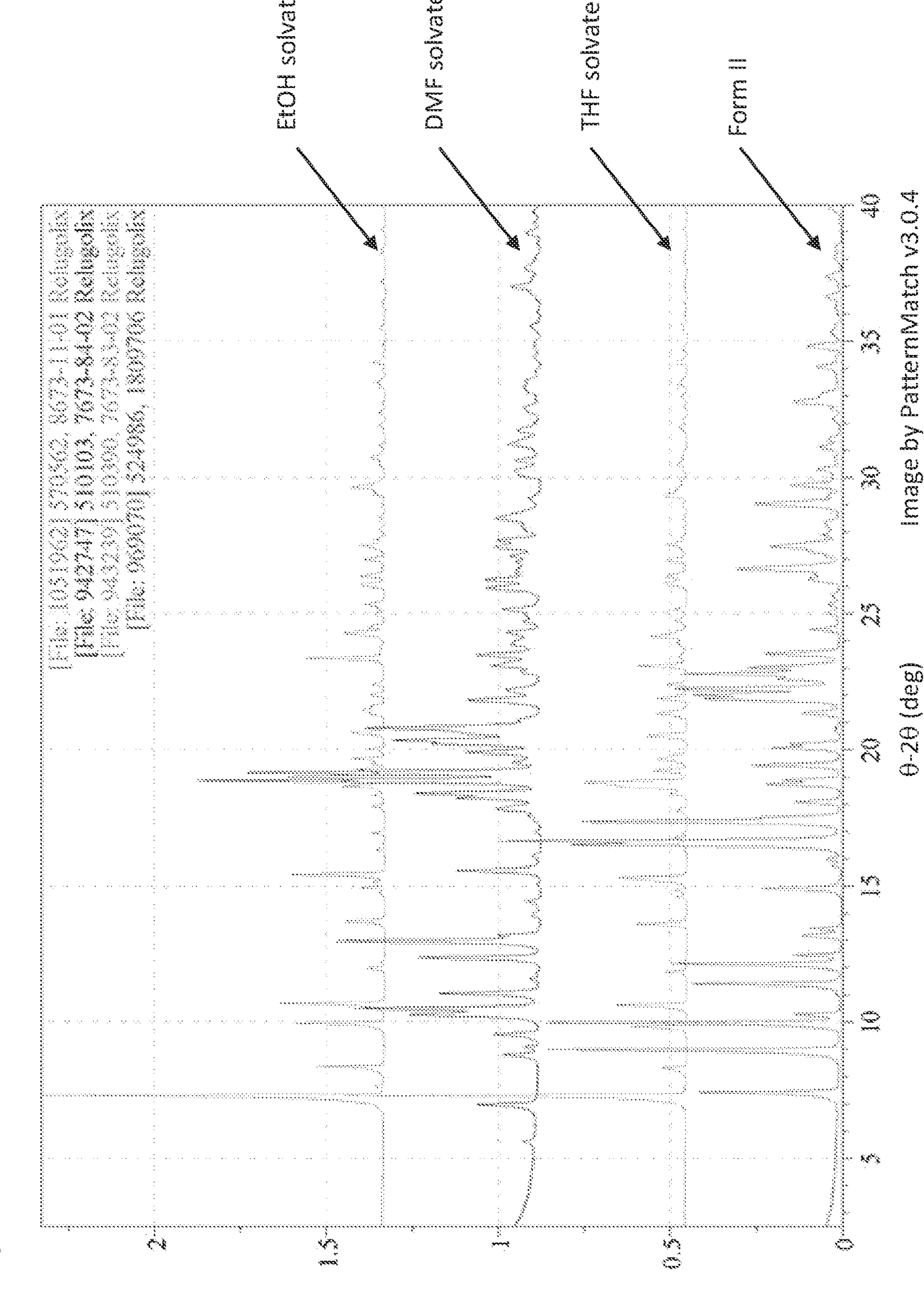
FIG. 2 depicts and overlays the powder X-ray diffraction patterns of Form XIV of Compound 1, Form XI of Compound 1, the THF solvate of Compound 1, and Form II of Compound 1.
Figure 3A:
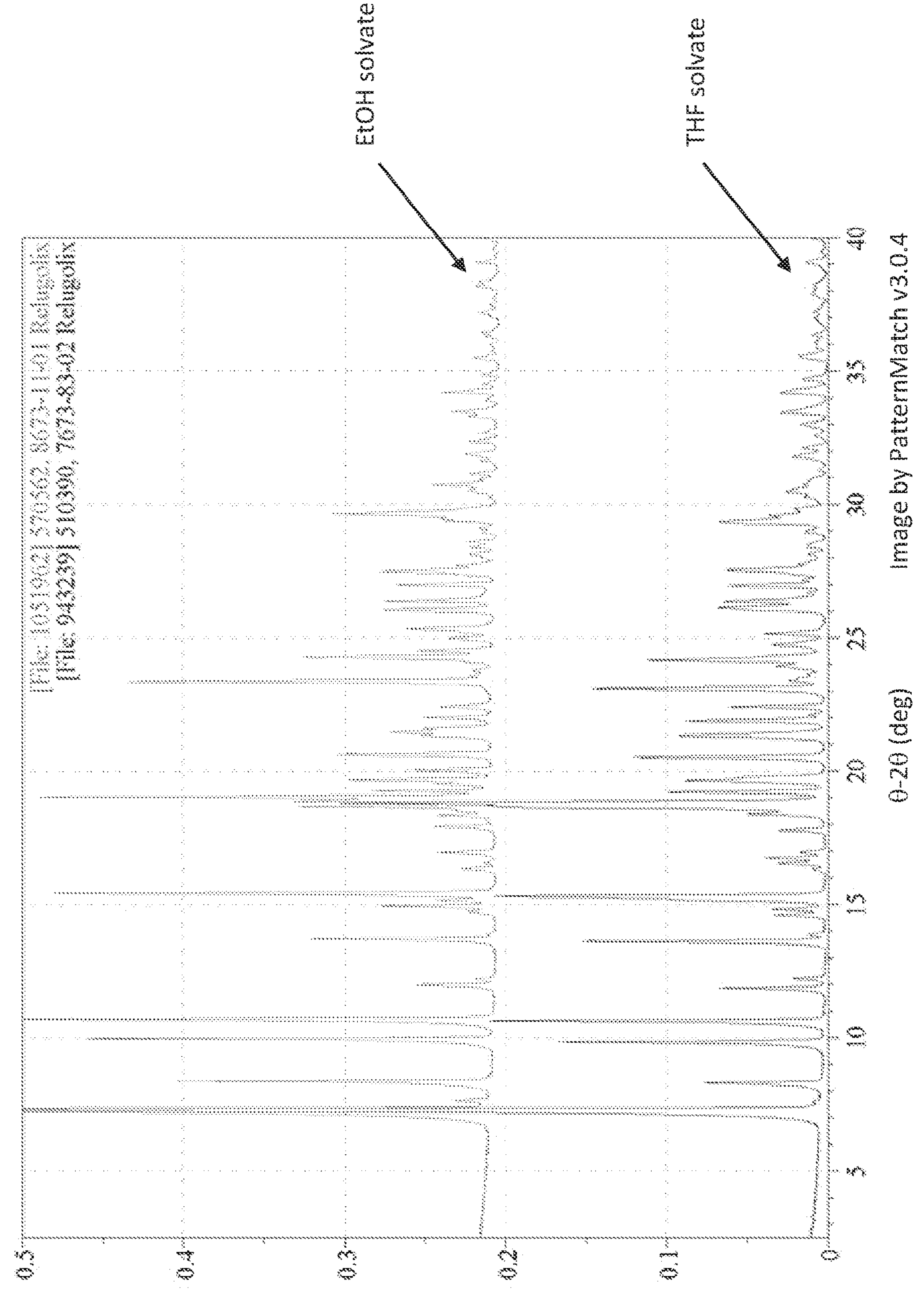
FIGS. 3A-C depict and overlay the powder X-ray diffraction patterns of Form XIV of Compound 1 and the THF solvate of Compound 1.
Figure 3B:
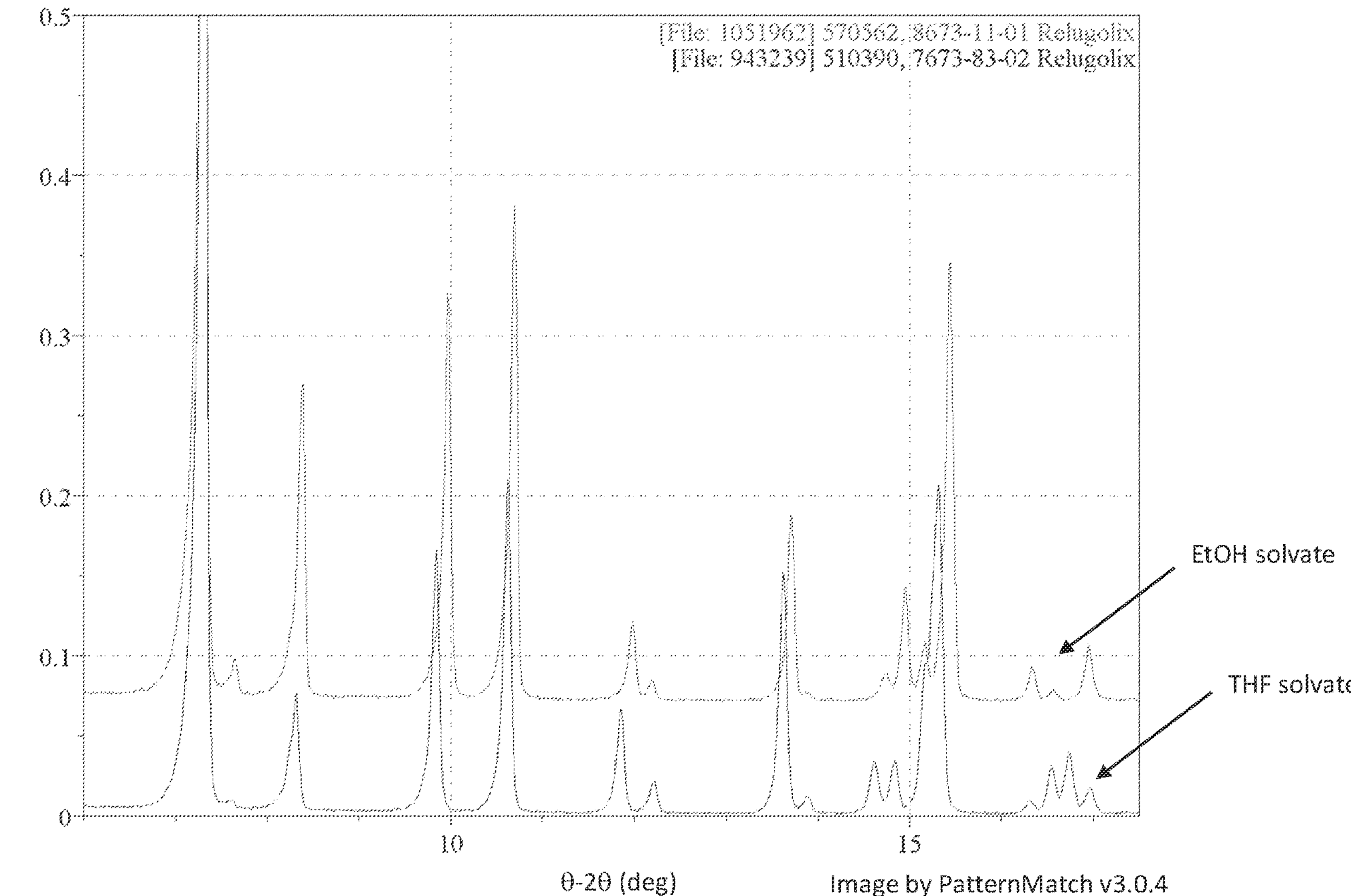
Figure 3C:
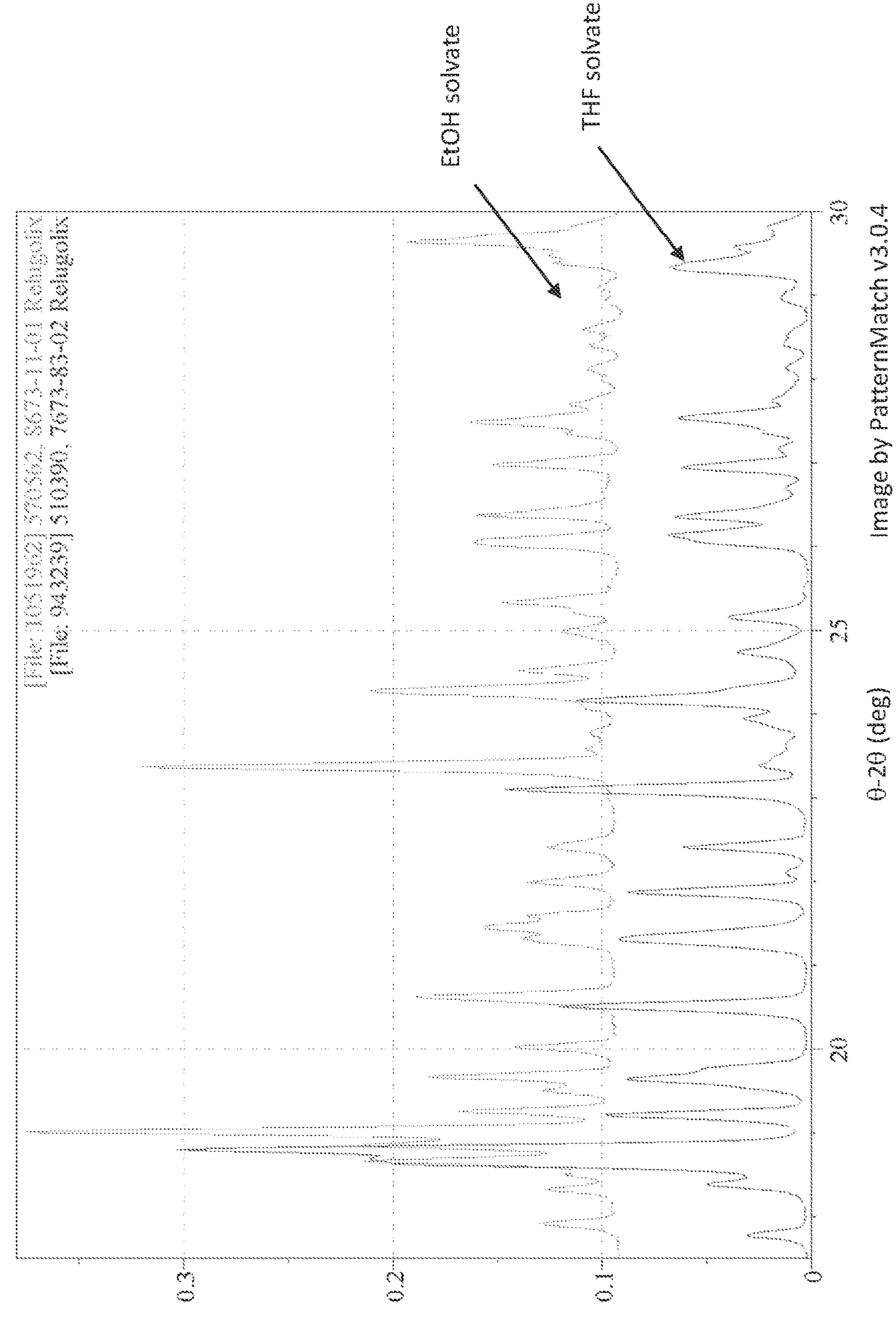

XRPD data for the crystalline Form XIV of Compound 1 disclosed herein was collected as detailed above. The XRPD pattern of Form XIV of Compound 1 is detailed in FIG. 1. The prominent peaks present in this XRPD pattern are listed in Table 1 and the observed peaks present in this XRPD pattern are listed in Table 2. All peak listings are in degrees 2θ±0.2° 2θ. The XRPD pattern was successfully indexed and the tentative unit cell parameters are provided in Table 4, below. The indexing of the XRPD pattern indicates that the material exists primarily or exclusively as a single crystalline phase. The XRPD pattern of shows that Form XIV of Compound 1 is isostructural with the tetrahydrofuran (THF) solvate of Compound 1 disclosed in U.S. Pat. No. 9,758,528. The XRPD patterns of Form XIV of Compound 1, Form XI of Compound 1, the THE solvate of Compound 1, and Form II of Compound 1 are shown and compared in FIG. 2. The XRPD patterns of Form XIV of Compound 1 and the tetrahydrofuran (THF) solvate of Compound 1 are shown and compared in FIGS. 3A-C.

TABLE 4

| Cell parameters for Form XIV of Compound 1 | |
|---|---|
| Bravais Type | Primitive monoclinic |
| a [Å] | 12.388 |
| b [Å] | 23.093 |
| c [Å] | 12.153 |
| α [deg] | 90 |
| β [deg] | 102.98 |
| γ [deg] | 90 |
| Vol. [$Å^3$/cell] | 3387.6 |
| Chiral Contents? | Not specified |
| Extinction Symbol | P 1 $2_1$/c 1 |
| Space Group(s) | $P2_1$/c (14) |

Thermal Analyses (DSC and TG) of Form XIV of Compound 1

Figure 4:
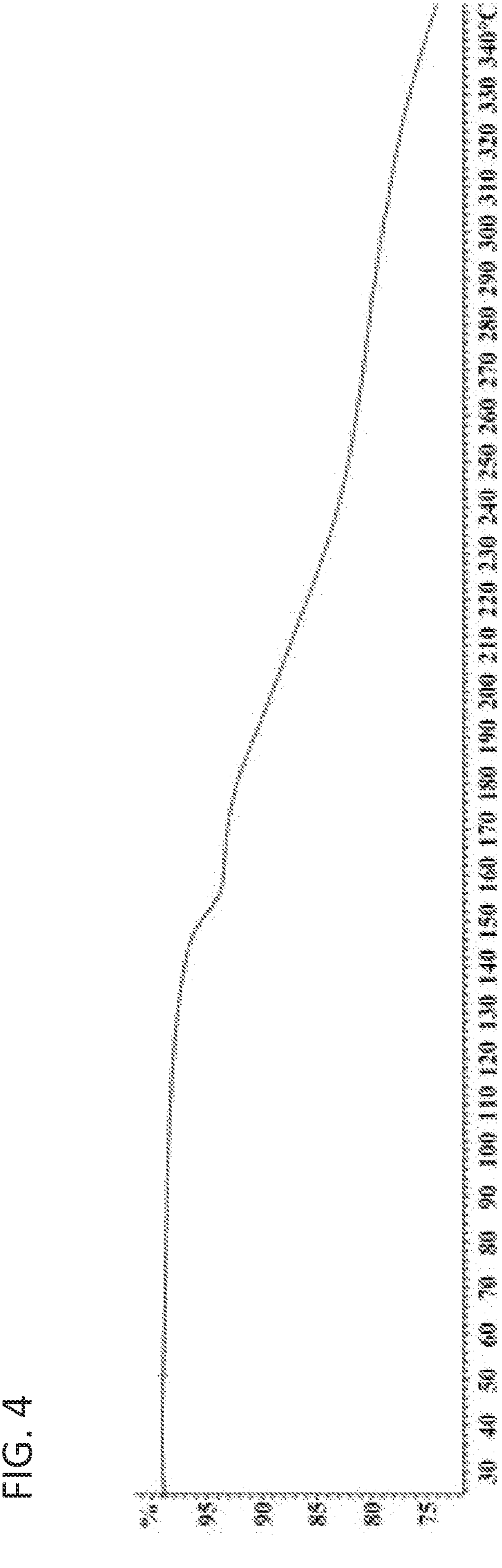
FIG. 4 depicts a thermogravimetric analysis of Form XIV of Compound 1, showing a step of approximately –6.036%.
Figure 5:
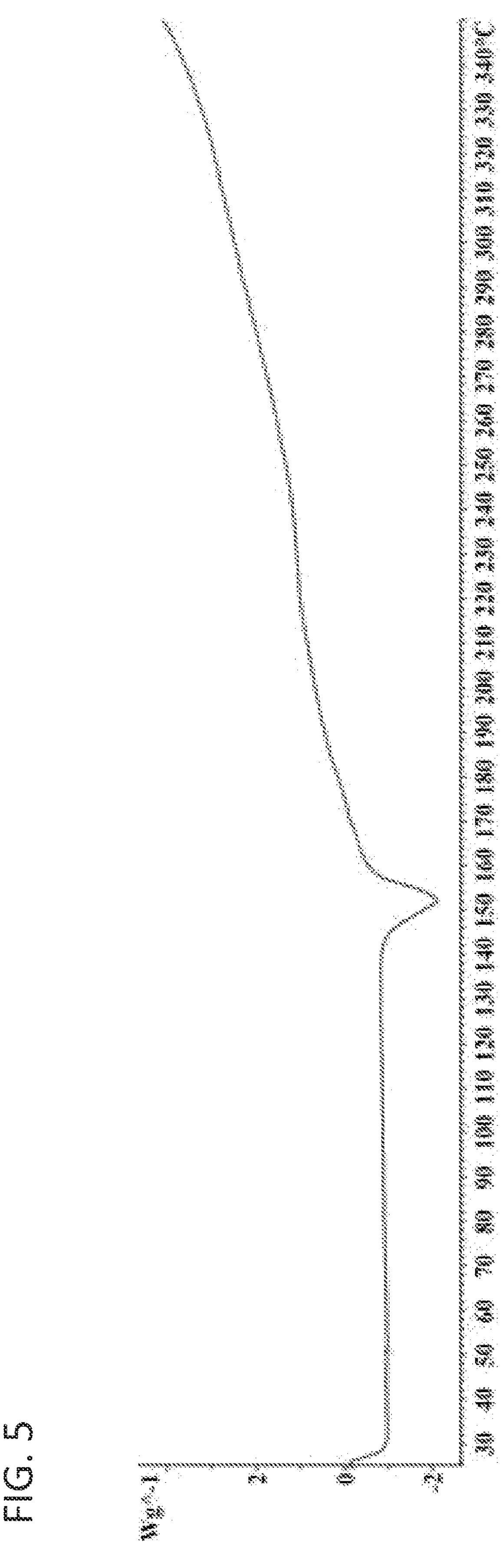
FIG. 5 depicts a differential scanning calorimetric analysis of Form XIV of Compound 1, showing an onset temperature of approximately 142.33° C. and a peak temperature of approximately 149.24° C.

The DSC and TG data for Form XIV of Compound 1 disclosed herein were collected as detailed above. The TG thermogram for Form XIV of Compound 1 is depicted in FIG. 4. The DSC thermogram for Form XIV of Compound 1 is depicted in FIG. 5. The thermal events in the DSC and TG of Form XIV of Compound 1 are compiled in Table 5, below. The TG thermogram indicated 6.0% weight loss from 49 to 171° C. and corresponds to 0.9 mol of ethanol. An endotherm was observed in the DSC thermogram with an onset temperature of 142° C.

TABLE 5

| DSC and TG thermal events for Form XIV of Compound 1 | |
|---|---|
| DSC | Endotherm at 149.24° C. (onset 142.3° C.) |
| TG | 6.0% wt. loss at 49-171° C. (corresponding to 0.9 mol of EtOH) |

$^1$H NMR Characterization of Form XIV of Compound 1

The $^1$H NMR spectrum of Form XIV of Compound 1 is depicted in FIGS. 6A-D. The spectrum is consistent with the structure of Compound 1 and indicates the presence of a trace amount of DMF and 1.15 mol of EtOH (relative to 1 mol of Compound 1).

Example 2: Additional Preparations and Characterization of Form XIV of Compound 1

Figure 7A:
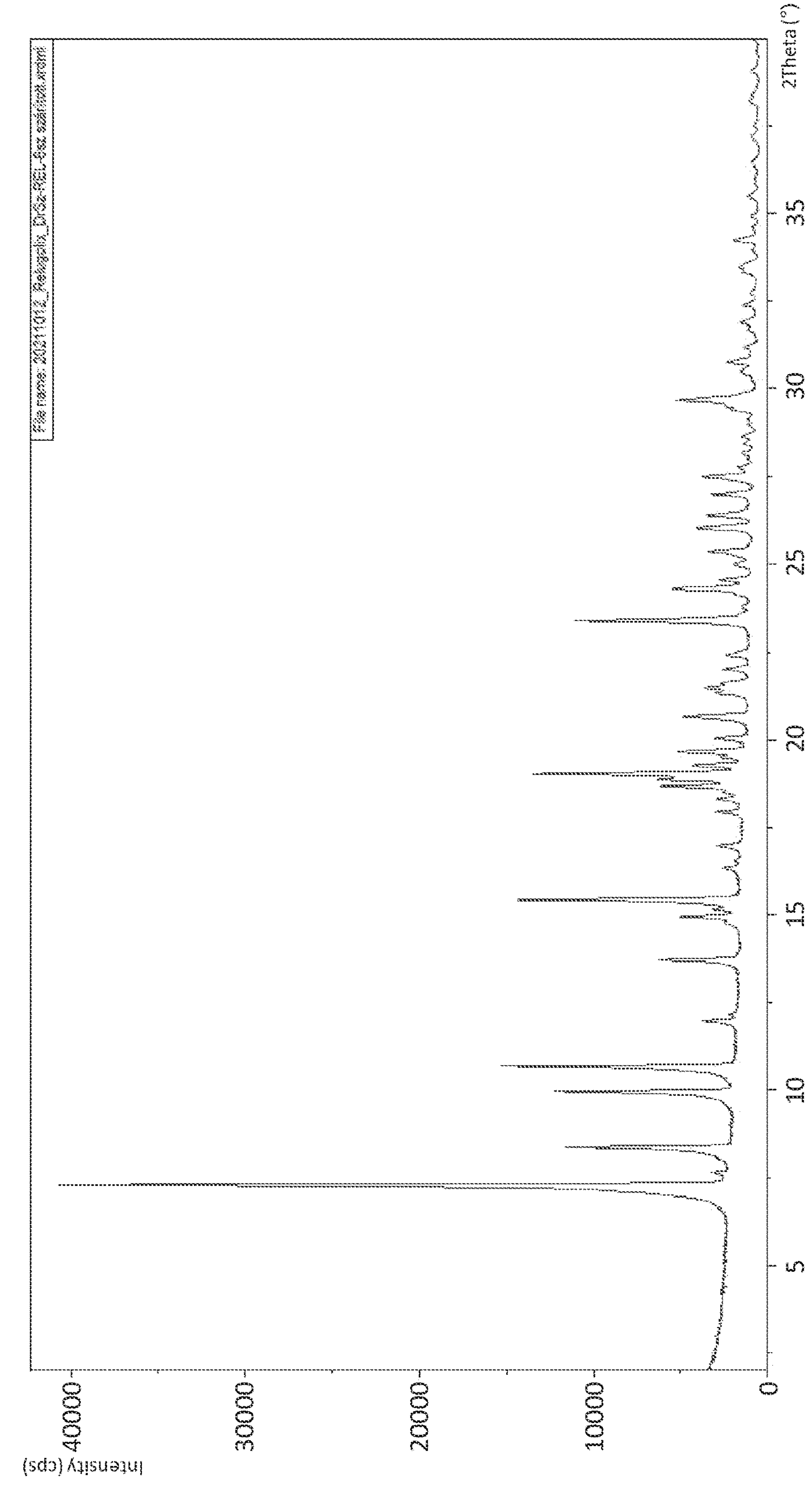
FIG. 7A and FIG. 7B show XRPD, TG, and DSC analyses of a sample preparation of Form XIV of Compound 1.
Figure 7B:
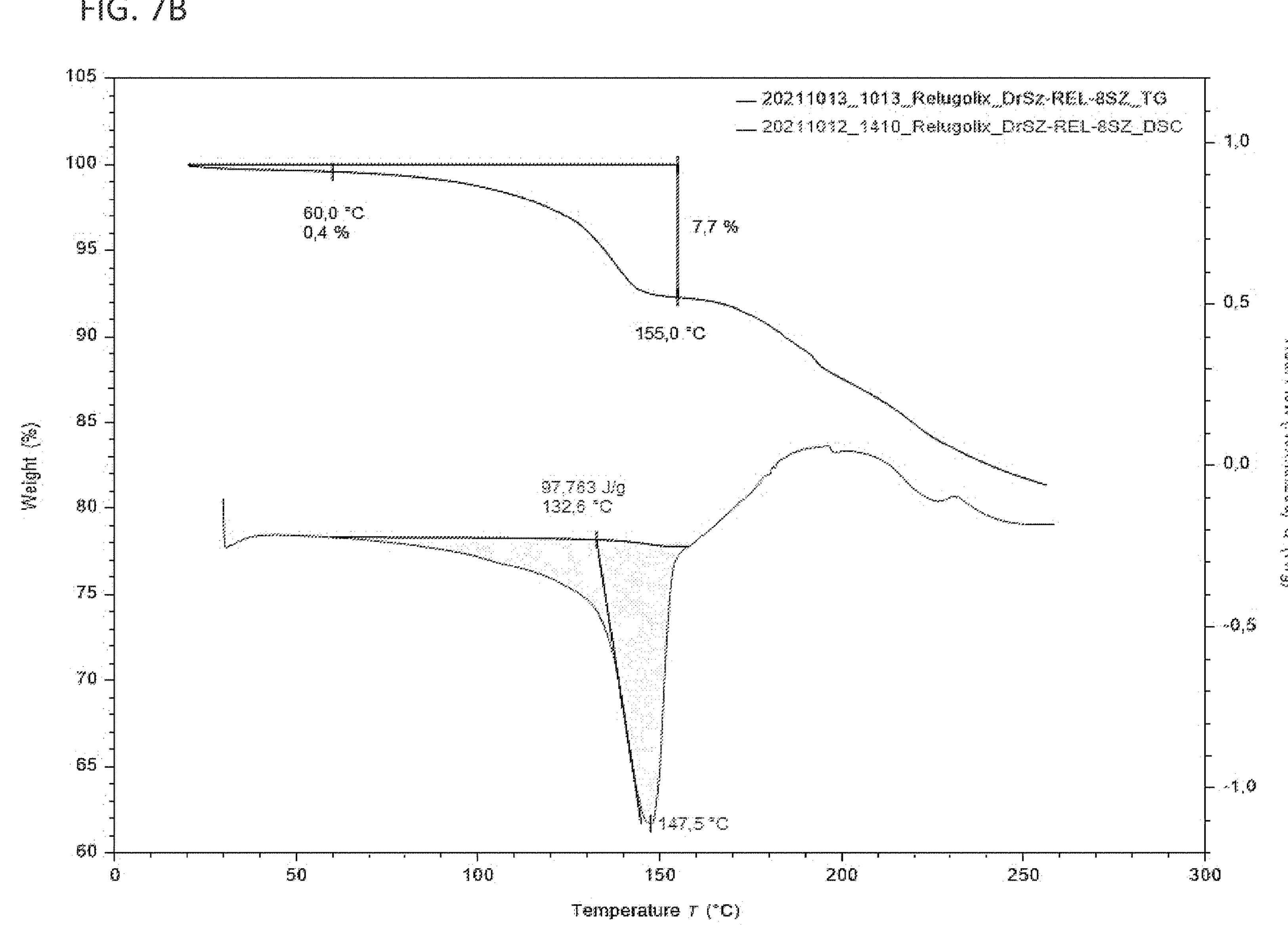

Example 2: Form XIV of Compound 1 was additionally prepared by dissolving Form I of Compound 1 (1.0 g) in abs. ethanol (78 ml) at reflux temperature. The solution was filtered through a 0.1 μm nylon filter into a 100 ml EasyMax reactor and the clear solution was cooled over approximately 30 minutes to 0° C. The resulted slurry was stirred for 3 hours and the solids were filtered. The obtained wet crystals were dried for 30 minutes at 40° C. in vacuum (500 mbar) under Nitrogen stream, providing 0.325 g of Form XIV of Compound 1. The sample was characterized by XRPD (FIG. 7A), TG-MS (FIG. 7B), DSC (FIG. 7C), and NMR. XRPD analysis is shown in Table 6.

TABLE 6

XRPD data of Form XIV of Compound 1

| Pos. [°2θ] | d-spacing [Å] | Height [cts] | Area [cts*°2θ] | FWHM Left [°2θ] | Rel. Int. [%] |
|---|---|---|---|---|---|
| 7.2975 | 12.11412 | 38729.21 | 1954.84 | 0.0512 | 100.00 |
| 7.6466 | 11.56180 | 1023.82 | 51.68 | 0.0512 | 2.64 |
| 8.3749 | 10.55799 | 9260.94 | 584.30 | 0.0640 | 23.91 |
| 9.9680 | 8.87386 | 10440.10 | 526.96 | 0.0512 | 26.96 |
| 10.6917 | 8.27476 | 12919.18 | 815.11 | 0.0640 | 33.36 |
| 11.9840 | 7.38518 | 1988.02 | 100.34 | 0.0512 | 5.13 |
| 13.7168 | 6.45588 | 4595.42 | 289.94 | 0.0640 | 11.87 |
| 14.9463 | 5.92749 | 3448.80 | 217.60 | 0.0640 | 8.90 |
| 15.1404 | 5.85193 | 1649.94 | 83.28 | 0.0512 | 4.26 |
| 15.4361 | 5.74047 | 12750.96 | 965.40 | 0.0768 | 32.92 |
| 16.3301 | 5.42817 | 1070.67 | 108.08 | 0.1023 | 2.76 |
| 16.9643 | 5.22666 | 1422.40 | 107.69 | 0.0768 | 3.67 |
| 17.9249 | 4.94864 | 1603.37 | 121.39 | 0.0768 | 4.14 |
| 18.3076 | 4.84606 | 1537.65 | 97.02 | 0.0640 | 3.97 |

TABLE 6-continued

XRPD data of Form XIV of Compound 1

| Pos. [°2θ] | d-spacing [Å] | Height [cts] | Area [cts*°2θ] | FWHM Left [°2θ] | Rel. Int. [%] |
|---|---|---|---|---|---|
| 18.6639 | 4.75436 | 4743.15 | 299.26 | 0.0640 | 12.25 |
| 18.8564 | 4.70625 | 5007.05 | 315.91 | 0.0640 | 12.93 |
| 19.0329 | 4.66300 | 12242.25 | 926.89 | 0.0768 | 31.61 |
| 19.2637 | 4.60765 | 2944.49 | 185.78 | 0.0640 | 7.60 |
| 19.4901 | 4.55462 | 1415.16 | 89.29 | 0.0640 | 3.65 |
| 19.6628 | 4.51502 | 3790.78 | 287.01 | 0.0768 | 9.79 |
| 20.0370 | 4.43155 | 1820.30 | 137.82 | 0.0768 | 4.70 |
| 20.6503 | 4.30129 | 3679.31 | 417.85 | 0.1151 | 9.50 |
| 21.2891 | 4.17364 | 1559.42 | 118.07 | 0.0768 | 4.03 |
| 21.4666 | 4.13954 | 2470.74 | 187.06 | 0.0768 | 6.38 |
| 21.6203 | 4.11046 | 1379.90 | 104.48 | 0.0768 | 3.56 |
| 21.9939 | 4.04147 | 1376.90 | 139.00 | 0.1023 | 3.56 |
| 22.4001 | 3.96909 | 1260.90 | 95.46 | 0.0768 | 3.26 |
| 23.3847 | 3.80415 | 9984.74 | 1007.95 | 0.1023 | 25.78 |
| 23.7870 | 3.74072 | 411.78 | 41.57 | 0.1023 | 1.06 |
| 24.3253 | 3.65914 | 4189.02 | 475.74 | 0.1151 | 10.82 |
| 24.5518 | 3.62589 | 1724.33 | 130.55 | 0.0768 | 4.45 |
| 25.0160 | 3.55966 | 898.69 | 113.40 | 0.1279 | 2.32 |
| 25.3525 | 3.51318 | 2435.58 | 122.94 | 0.0512 | 6.29 |
| 26.0325 | 3.42293 | 2997.50 | 378.25 | 0.1279 | 7.74 |
| 26.3885 | 3.37756 | 2497.07 | 157.55 | 0.0640 | 6.45 |
| 26.9861 | 3.30409 | 2252.75 | 142.13 | 0.0640 | 5.82 |
| 27.4831 | 3.24546 | 2789.73 | 211.22 | 0.0768 | 7.20 |
| 27.7520 | 3.21463 | 791.67 | 79.92 | 0.1023 | 2.04 |
| 28.1447 | 3.17066 | 464.45 | 70.33 | 0.1535 | 1.20 |
| 29.0490 | 3.07398 | 146.10 | 29.50 | 0.2047 | 0.38 |
| 29.6603 | 3.01201 | 4468.46 | 338.32 | 0.0768 | 11.54 |
| 30.4595 | 2.93477 | 691.46 | 104.70 | 0.1535 | 1.79 |
| 30.7530 | 2.90743 | 1550.15 | 97.80 | 0.0640 | 4.00 |
| 31.1859 | 2.86805 | 573.91 | 57.94 | 0.1023 | 1.48 |
| 31.9192 | 2.80382 | 737.15 | 93.02 | 0.1279 | 1.90 |
| 32.3962 | 2.76362 | 711.65 | 53.88 | 0.0768 | 1.84 |
| 32.7290 | 2.73627 | 233.66 | 23.59 | 0.1023 | 0.60 |
| 33.4871 | 2.67604 | 902.59 | 159.45 | 0.1791 | 2.33 |
| 34.2221 | 2.62024 | 1278.96 | 80.69 | 0.0640 | 3.30 |
| 34.9177 | 2.56961 | 279.04 | 28.17 | 0.1023 | 0.72 |

Figure 8A:
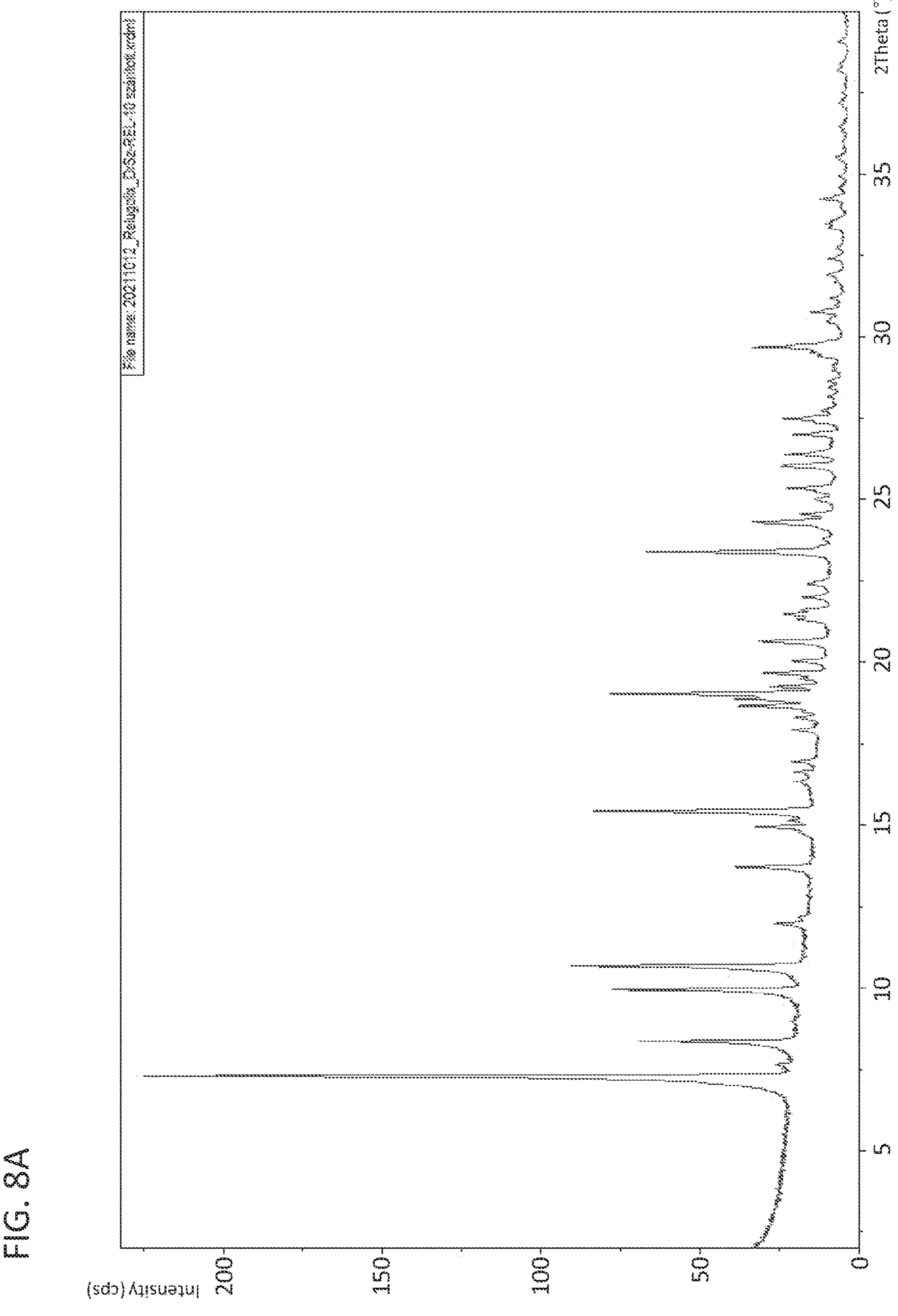
FIG. 8A and FIG. 8B show XRPD, TG, and DSC analyses of a sample preparation of Form XIV of Compound 1.
Figure 8B:
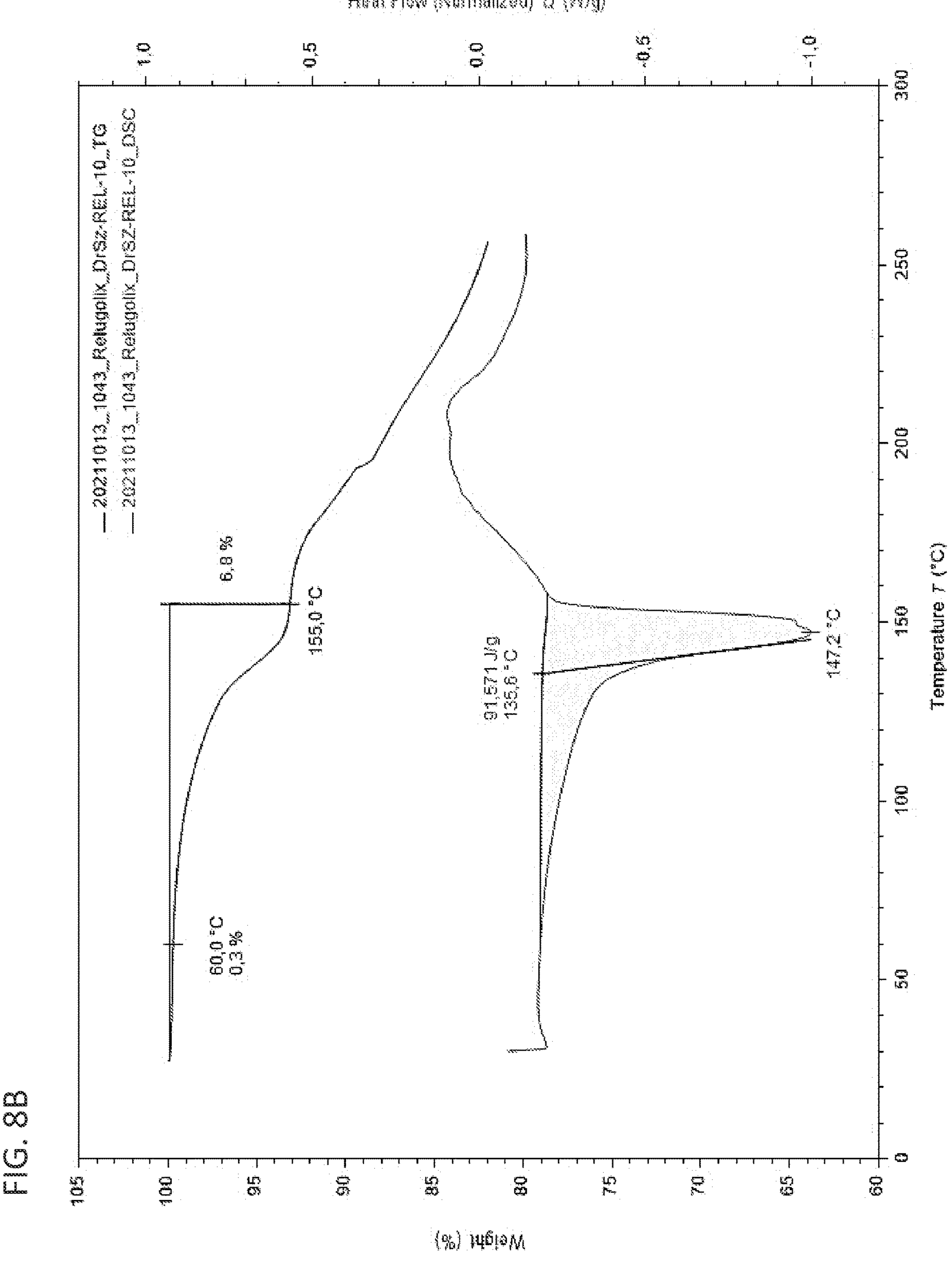

Form XIV of Compound 1 was additionally prepared by dissolving Form I of Compound 1 (1.0 g) in abs. ethanol (130 ml) at reflux temperature. The clear solution was cooled in over about 30 minutes to 0° C. The resulting slurry was stirred for 3 hours and the solids were filtered. The obtained wet crystals were dried for 30 minutes at 40° C. in vacuum (500 mbar) under a stream of nitrogen, affording 0.533 g of Form XIV of Compound 1. The sample was characterized by XRPD (FIG. 8A), TG and DSC (FIG. 8B, TG thermogram indicated ca. 6.5% weight loss from 60 to 155° C. and corresponds to 0.94 mol of ethanol, and an endothermic peak on the DSC was observed at 147.2° C.), and NMR (spectrum is consistent with the structure of Compound 1 and indicates the presence of 0.98 mol of EtOH relative to 1 mol of Compound 1). XRPD analysis is shown in Table 7.

TABLE 7

XRPD data of Form XIV of Compound 1

| Pos. [°2θ] | d-spacing [Å] | Height [cts] | Area [cts*°2θ] | FWHM Left [°2θ] | Rel. Int. [%] |
|---|---|---|---|---|---|
| 7.2965 | 12.11570 | 22166.78 | 1118.86 | 0.0512 | 100.00 |
| 7.6384 | 11.57418 | 533.86 | 40.42 | 0.0768 | 2.41 |
| 8.3724 | 10.56103 | 5316.05 | 335.41 | 0.0640 | 23.98 |
| 9.9691 | 8.87287 | 6130.01 | 309.41 | 0.0512 | 27.65 |
| 10.6904 | 8.27574 | 7655.62 | 483.02 | 0.0640 | 34.54 |
| 11.9786 | 7.38853 | 1085.28 | 54.78 | 0.0512 | 4.90 |
| 13.7124 | 6.45795 | 2654.96 | 167.51 | 0.0640 | 11.98 |
| 14.9508 | 5.92572 | 2021.46 | 127.54 | 0.0640 | 9.12 |

TABLE 7-continued

XRPD data of Form XIV of Compound 1

| Pos. [°2θ] | d-spacing [Å] | Height [cts] | Area [cts*°2θ] | FWHM Left [°2θ] | Rel. Int. [%] |
|---|---|---|---|---|---|
| 15.1455 | 5.84995 | 850.19 | 53.64 | 0.0640 | 3.84 |
| 15.4355 | 5.74068 | 7531.33 | 570.21 | 0.0768 | 33.98 |
| 16.3239 | 5.43021 | 696.87 | 52.76 | 0.0768 | 3.14 |
| 16.6419 | 5.32717 | 746.88 | 37.70 | 0.0512 | 3.37 |
| 16.9640 | 5.22673 | 864.54 | 54.55 | 0.0640 | 3.90 |
| 17.9280 | 4.94782 | 935.28 | 59.01 | 0.0640 | 4.22 |
| 18.3006 | 4.84790 | 832.84 | 52.55 | 0.0640 | 3.76 |
| 18.6628 | 4.75463 | 2790.11 | 176.04 | 0.0640 | 12.59 |
| 18.8602 | 4.70530 | 2844.75 | 179.48 | 0.0640 | 12.83 |
| 19.0315 | 4.66334 | 7348.98 | 556.41 | 0.0768 | 33.15 |
| 19.2566 | 4.60933 | 1737.16 | 109.60 | 0.0640 | 7.84 |
| 19.4894 | 4.55479 | 776.57 | 39.20 | 0.0512 | 3.50 |
| 19.6620 | 4.51519 | 2110.40 | 159.78 | 0.0768 | 9.52 |
| 20.0357 | 4.43181 | 1072.58 | 81.21 | 0.0768 | 4.84 |
| 20.6451 | 4.30236 | 2170.44 | 191.72 | 0.0895 | 9.79 |
| 21.3106 | 4.16948 | 959.33 | 72.63 | 0.0768 | 4.33 |
| 21.4712 | 4.13867 | 1486.61 | 93.80 | 0.0640 | 6.71 |
| 21.6127 | 4.11187 | 750.80 | 37.90 | 0.0512 | 3.39 |
| 21.9987 | 4.04060 | 859.04 | 54.20 | 0.0640 | 3.88 |
| 22.3933 | 3.97028 | 738.67 | 37.28 | 0.0512 | 3.33 |
| 23.3886 | 3.80353 | 6156.16 | 466.09 | 0.0768 | 27.77 |
| 23.7884 | 3.74050 | 245.64 | 24.80 | 0.1023 | 1.11 |
| 24.3286 | 3.65866 | 2655.48 | 268.07 | 0.1023 | 11.98 |
| 24.5478 | 3.62648 | 1067.27 | 67.34 | 0.0640 | 4.81 |
| 25.0153 | 3.55975 | 601.85 | 30.38 | 0.0512 | 2.72 |
| 25.3511 | 3.51336 | 1531.09 | 77.28 | 0.0512 | 6.91 |
| 26.0089 | 3.42598 | 1640.10 | 186.26 | 0.1151 | 7.40 |
| 26.3837 | 3.37815 | 1639.16 | 82.74 | 0.0512 | 7.39 |
| 26.9898 | 3.30365 | 1421.20 | 71.73 | 0.0512 | 6.41 |
| 27.4830 | 3.24549 | 1768.13 | 111.56 | 0.0640 | 7.98 |
| 27.7417 | 3.21580 | 479.81 | 48.44 | 0.1023 | 2.16 |
| 28.1716 | 3.16770 | 267.13 | 20.23 | 0.0768 | 1.21 |
| 28.4321 | 3.13927 | 253.79 | 19.22 | 0.0768 | 1.14 |
| 28.6345 | 3.11753 | 286.50 | 21.69 | 0.0768 | 1.29 |
| 29.0512 | 3.07375 | 89.48 | 13.55 | 0.1535 | 0.40 |
| 29.3843 | 3.03966 | 650.52 | 32.83 | 0.0512 | 2.93 |
| 29.6654 | 3.01150 | 2868.01 | 144.76 | 0.0512 | 12.94 |
| 30.4666 | 2.93411 | 359.19 | 36.26 | 0.1023 | 1.62 |
| 30.7600 | 2.90678 | 984.25 | 49.68 | 0.0512 | 4.44 |
| 31.1770 | 2.86885 | 335.69 | 16.94 | 0.0512 | 1.51 |
| 31.9086 | 2.80473 | 443.89 | 22.41 | 0.0512 | 2.00 |
| 32.3941 | 2.76379 | 429.38 | 43.35 | 0.1023 | 1.94 |

What is claimed:

1. A crystalline form of an ethanol solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XIV of Compound 1.

2. The crystalline form of claim 1, characterized by an X-ray powder diffraction pattern comprising at least three peaks selected from 7.31°, 8.38°, 9.96°, 10.69°, 15.43°, 19.02°, and 23.36° 2θ±0.2° 2θ.

3. The crystalline form of claim 1, characterized by an X-ray powder diffraction pattern comprising at least five peaks selected from 7.31°, 8.38°, 9.96°, 10.69°, 15.43°, 19.02°, and 23.36° 2θ±0.2° 2θ.

4. The crystalline form of claim 1, characterized by an X-ray powder diffraction pattern comprising peaks at 7.31°, 8.38°, 9.96°, 10.69°, 15.43°, 19.02°, and 23.36° 2θ±0.2° 2θ.

5. The crystalline form of claim 1, characterized by an X-ray powder diffraction pattern substantially the same as the pattern shown in FIG. 1.

6. The crystalline form of claim 1, characterized by a thermogravimetric (TG) thermogram indicating continuous weight loss of about 6.0% between about 49° C. and about 172° C.

7. The crystalline form of claim 1, characterized by a TG thermogram substantially the same as the pattern shown in FIG. 4.

8. The crystalline form of claim 1, characterized by a differential scanning calorimetry (DSC) thermogram comprising an endothermic peak between about 147° C. and about 150° C.

9. The crystalline form of claim 1, characterized by a DSC thermogram comprising an endothermic peak at about 149° C.

10. The crystalline form of claim 1, characterized by a DSC thermogram substantially the same as the pattern shown in FIG. 5.

11. The crystalline form of claim 1, characterized by an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å.

12. The crystalline form of claim 1, characterized by having at least two of the following:

a) an X-ray powder diffraction pattern comprising at least three peaks selected from 7.31°, 8.38°, 9.96°, 10.69°, 15.43°, 19.02°, and 23.36° 2θ±0.2° 2θ;

b) an X-ray powder diffraction pattern comprising at least three peaks having approximate d-spacing value selected from 3.805 Å, 4.662 Å, 5.738 Å, 8.269 Å, 8.874 Å, 10.543 Å, and 12.083 Å; and c) an endothermic peak at about 149° C. as measured by DSC.

13. The crystalline form of claim 1, wherein said crystalline form is substantially free of tetrahydrofuran (THF).

14. A pharmaceutical composition comprising the crystalline form of claim 1.

15. The pharmaceutical composition of claim 14, wherein said composition is substantially free of (THF).

16. A method for preparing the crystalline form of claim 1 comprising:

a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in dimethylformamide (DMF) to form a solution;

b) adding the solution of step a) to ethanol to form a second solution;

c) stirring the second solution to generate a suspension; and d) isolating solids from the suspension to afford Form XIV of Compound 1.

17. The method of claim 16, wherein the second solution is cooled to between about −10° C. and −25° C.

18. The method of claim 16, wherein the second solution of step b) is cooled to between about −10° C. and −25° C., for 1 day.

19. The method of claim 16, wherein the stirring of step c) is carried between about −10° C. and −25° C.

20. The method of claim 16, wherein the isolating of step d) is accomplished using syringe filtration.

21. A method for preparing the crystalline form of claim 1 comprising:

a) dissolving a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in ethanol (EtOH) to form a solution;

b) cooling the solution of step a);

c) stirring the cooled solution to generate a suspension; and d) isolating solids from the suspension to afford Form XIV of Compound 1.

22. The method of claim 21, wherein the solution of step a) is cooled to between about 5° C. and −10° C.

23. The method of claim 21, wherein the stirring of step c) is carried between about 5° C. and −10° C.

24. The method of claim 21, wherein the isolating of step d) is accomplished using filtration.

* * * * *